US011103706B2

(12) United States Patent
Sachs et al.

(10) Patent No.: US 11,103,706 B2
(45) Date of Patent: *Aug. 31, 2021

(54) SYSTEMS AND METHODS FOR ENHANCING FUNCTION OF SPINE STABILIZATION MUSCLES ASSOCIATED WITH A SPINE SURGERY INTERVENTION

(71) Applicant: MAINSTAY MEDICAL LIMITED, Swords (IE)

(72) Inventors: Dan Sachs, Minneapolis, MN (US); Prashant Brijmohansingh Rawat, Blaine, MN (US); Peter Andrew Crosby, Blaine, MN (US); Jason Hannon, Swords (IE)

(73) Assignee: Mainstay Medical Limited, Dublin (IE)

( * ) Notice: Subject to any disclaimer, the term of this patent is extended or adjusted under 35 U.S.C. 154(b) by 209 days.

This patent is subject to a terminal disclaimer.

(21) Appl. No.: 16/264,632

(22) Filed: Jan. 31, 2019

(65) Prior Publication Data

US 2019/0167995 A1 Jun. 6, 2019

Related U.S. Application Data

(63) Continuation-in-part of application No. 15/994,730, filed on Apr. 3, 2018, which is a continuation of
(Continued)

(51) Int. Cl.
*A61N 1/18* (2006.01)
*A61N 1/36* (2006.01)
(Continued)

(52) U.S. Cl.
CPC ..... *A61N 1/36071* (2013.01); *A61N 1/36067* (2013.01); *A61N 1/36146* (2013.01);
(Continued)

(58) Field of Classification Search
CPC .............. A61N 1/3604; A61N 1/36062; A61N 1/36071; A61N 1/36103
See application file for complete search history.

(56) References Cited

U.S. PATENT DOCUMENTS

| 3,077,884 A | 2/1963 | Batrow et al. |
| 3,416,534 A | 12/1968 | Quinn |
| (Continued) | | |

FOREIGN PATENT DOCUMENTS

| CN | 1211930 A | 3/1999 |
| CN | 1211930 C | 7/2005 |
| (Continued) | | |

OTHER PUBLICATIONS

Airaksinen et al., "Chapter 4. European guidelines for the management of chronic nonspecific low back pain," European spine journal [I: official publication of the European Spine Society, the European Spinal Deformity Society, and the European Section of the Cervical Spine Research Society 15 Suppl 2 (2006):5192-300. http://www.ncbi.nlm.nih.gov/pubmed/16550448.
(Continued)

*Primary Examiner* — Allen Porter
(74) *Attorney, Agent, or Firm* — Eversheds Sutherland (US) LLP; Christopher C. Bolten; Albert K. Heng

(57) ABSTRACT

A method for enhancing muscle function of skeletal muscles in connection with a planned spine surgery intervention in a patient's back is provided. The method includes implanting one or more electrodes in or adjacent to tissue associated with one or more skeletal muscles within a back of a patient, the one or more electrodes in electrical communication with a pulse generator programmed for enhancing muscle function of the one or more skeletal muscles. Electrical stimulation is delivered, according to the programming during a time period associated with the planned spine surgery intervention, from the pulse generator to the tissue associated
(Continued)

with the one or more skeletal muscles via the one or more electrodes, thereby improving neuromuscular control system performance of the one or more spine stabilizing muscles in connection with the planned spine surgery intervention to reduce the patient's recovery time associated with the planned spine surgery intervention.

15 Claims, 20 Drawing Sheets

Related U.S. Application Data application No. 15/299,399, filed on Oct. 20, 2016, now Pat. No. 10,016,603, which is a continuation of application No. 14/792,430, filed on Jul. 6, 2015, now Pat. No. 9,474,906, which is a continuation of application No. 14/061,614, filed on Oct. 23, 2013, now Pat. No. 9,072,897, which is a continuation-in-part of application No. 13/858,809, filed on Apr. 8, 2013, now Pat. No. 8,606,358, which is a continuation of application No. 12/075,174, filed on Mar. 10, 2008, now Pat. No. 8,428,728.

(60) Provisional application No. 60/905,979, filed on Mar. 9, 2007.

(51) Int. Cl.
*A61N 1/372* (2006.01)
*A61N 2/00* (2006.01)
*A61N 2/02* (2006.01)
*A61N 2/06* (2006.01)
*A61N 1/05* (2006.01)

(52) U.S. Cl.
CPC ......... *A61N 1/37229* (2013.01); *A61N 2/008* (2013.01); *A61N 2/02* (2013.01); *A61N 1/0551* (2013.01); *A61N 1/0558* (2013.01); *A61N 1/36003* (2013.01); *A61N 1/36125* (2013.01); *A61N 1/36157* (2013.01); *A61N 1/36167* (2013.01); *A61N 1/36175* (2013.01); *A61N 1/36185* (2013.01); *A61N 1/37247* (2013.01); *A61N 2/06* (2013.01)

(56) References Cited

U.S. PATENT DOCUMENTS

| | | |
|---|---|---|
| 3,710,777 A | 1/1973 | Sparks |
| 3,754,555 A | 8/1973 | Schmitt |
| 3,875,947 A | 4/1975 | Jula et al. |
| 3,893,463 A | 7/1975 | Williams |
| 3,902,501 A | 9/1975 | Citron et al. |
| 3,976,082 A | 8/1976 | Schmitt |
| 3,999,551 A | 12/1976 | Spitz et al. |
| 4,010,757 A | 3/1977 | Jula et al. |
| 4,026,301 A | 5/1977 | Friedman et al. |
| 4,031,899 A | 6/1977 | Renirie |
| 4,149,528 A | 4/1979 | Murphy |
| 4,235,246 A | 11/1980 | Weiss |
| 4,269,198 A | 5/1981 | Stokes |
| 4,342,317 A | 8/1982 | Axelgaard |
| 4,408,609 A | 10/1983 | Axelgaard |
| 4,418,693 A | 12/1983 | Leveen et al. |
| 4,528,984 A | 7/1985 | Morawetz et al. |
| 4,549,556 A | 10/1985 | Tarjan et al. |
| 4,574,806 A | 3/1986 | McCarthy |
| 4,658,835 A | 4/1987 | Pohndorf |
| 4,832,687 A | 5/1989 | Smith, III |
| 4,917,093 A | 4/1990 | Dufresne et al. |
| 5,069,680 A | 12/1991 | Grandjean |
| 5,199,430 A | 4/1993 | Fang et al. |
| 5,215,088 A | 6/1993 | Normann et al. |
| 5,273,053 A | 12/1993 | Pohndorf |
| 5,300,108 A | 4/1994 | Rebell et al. |
| 5,330,515 A | 7/1994 | Rutecki et al. |
| 5,376,108 A | 12/1994 | Collins et al. |
| 5,496,345 A | 3/1996 | Kieturakis et al. |
| 5,501,452 A | 3/1996 | Halvorson |
| 5,507,788 A | 4/1996 | Lieber |
| 5,522,854 A | 6/1996 | Ideker et al. |
| 5,569,183 A | 10/1996 | Kieturakis |
| 5,638,825 A | 6/1997 | Yamazaki et al. |
| 5,733,307 A | 3/1998 | Dinsdale |
| 5,741,321 A | 4/1998 | Brennen |
| 5,760,341 A | 6/1998 | Laske et al. |
| 5,782,841 A | 7/1998 | Ritz et al. |
| 5,807,234 A | 9/1998 | Bui et al. |
| 5,873,900 A | 2/1999 | Maurer et al. |
| 5,897,584 A | 4/1999 | Herman |
| 5,916,172 A | 6/1999 | Hodges et al. |
| 5,957,968 A | 9/1999 | Belden et al. |
| 6,104,957 A | 8/2000 | Alo et al. |
| 6,119,516 A | 9/2000 | Hock |
| 6,314,325 B1 | 11/2001 | Fitz |
| 6,319,241 B1 | 11/2001 | King et al. |
| 6,324,414 B1 | 11/2001 | Gibbons et al. |
| 6,366,819 B1 | 4/2002 | Stokes |
| 6,381,496 B1 | 4/2002 | Meadows et al. |
| 6,406,421 B1 | 6/2002 | Grandjean et al. |
| 6,473,654 B1 | 10/2002 | Chinn |
| 6,516,227 B1 | 2/2003 | Meadows et al. |
| 6,527,787 B1 | 3/2003 | Fogarty et al. |
| 6,565,594 B1 | 5/2003 | Herweck et al. |
| 6,600,954 B2 | 7/2003 | Cohen et al. |
| 6,600,956 B2 | 7/2003 | Maschino et al. |
| 6,605,094 B1 | 8/2003 | Mann et al. |
| 6,671,557 B1 | 12/2003 | Gliner |
| 6,735,474 B1 | 5/2004 | Loeb et al. |
| 6,839,594 B2 | 1/2005 | Cohen et al. |
| 6,845,271 B2 | 1/2005 | Fang et al. |
| 6,862,479 B1 | 3/2005 | Whitehurst et al. |
| 7,018,384 B2 | 3/2006 | Skakoon |
| 7,096,070 B1 | 8/2006 | Jenkins et al. |
| 7,206,641 B2 | 4/2007 | Ignagni et al. |
| 7,218,970 B2 | 5/2007 | Ley et al. |
| 7,239,918 B2 | 7/2007 | Strother et al. |
| 7,286,879 B2 | 10/2007 | Wallace |
| 7,317,948 B1 | 1/2008 | King et al. |
| 7,324,852 B2 | 1/2008 | Barolat et al. |
| 7,324,853 B2 | 1/2008 | Ayal et al. |
| 7,337,005 B2 | 2/2008 | Kim et al. |
| 7,337,006 B2 | 2/2008 | Kim et al. |
| 7,369,894 B2 | 5/2008 | Gerber |
| 7,389,149 B2 | 6/2008 | Rossing et al. |
| 7,444,181 B2 | 10/2008 | Shi et al. |
| 7,447,546 B2 | 11/2008 | Kim et al. |
| 7,450,993 B2 | 11/2008 | Kim et al. |
| 7,489,561 B2 | 2/2009 | Armstrong et al. |
| 7,493,175 B2 | 2/2009 | Cates et al. |
| 7,499,746 B2 | 3/2009 | Buhlmann et al. |
| 7,502,651 B2 | 3/2009 | Kim et al. |
| 7,515,971 B1 | 4/2009 | Doan |
| 7,580,753 B2 | 8/2009 | Kim et al. |
| 7,668,598 B2 | 2/2010 | Herregraven et al. |
| 7,684,866 B2 | 3/2010 | Fowler et al. |
| 7,708,763 B2 | 5/2010 | Selover et al. |
| 7,761,166 B2 | 7/2010 | Giftakis et al. |
| 7,792,591 B2 | 9/2010 | Rooney et al. |
| 7,797,053 B2 | 9/2010 | Atkinson et al. |
| 7,813,803 B2 | 10/2010 | Heruth et al. |
| 7,908,015 B2 | 3/2011 | Lazeroms et al. |
| 7,917,230 B2 | 3/2011 | Bly |
| 7,930,039 B2 | 4/2011 | Olson |
| 7,981,144 B2 | 7/2011 | Geist et al. |
| 8,016,846 B2 | 9/2011 | McFarlin et al. |
| 8,065,020 B2 | 11/2011 | Ley et al. |
| 8,082,039 B2 | 12/2011 | Kim et al. |
| 8,170,690 B2 | 5/2012 | Morgan et al. |
| 8,229,565 B2 | 7/2012 | Kim et al. |
| 8,229,656 B2 | 7/2012 | Ikushima et al. |

(56) References Cited

U.S. PATENT DOCUMENTS

| | | |
|---|---|---|
| 8,249,701 B2 | 8/2012 | Imran et al. |
| 8,249,713 B2 | 8/2012 | Fang et al. |
| 8,321,021 B2 | 11/2012 | Kisker et al. |
| 8,380,318 B2 | 2/2013 | Kishawi et al. |
| 8,386,045 B2 | 2/2013 | Zhao et al. |
| 8,391,966 B2 | 3/2013 | Luo et al. |
| 8,409,233 B1 | 4/2013 | Chinn et al. |
| 8,428,728 B2 | 4/2013 | Sachs |
| 8,463,383 B2 | 6/2013 | Sakai et al. |
| 8,498,697 B2 | 7/2013 | Yong et al. |
| 8,606,358 B2 | 12/2013 | Sachs |
| 8,798,005 B1 | 8/2014 | Vargantwar et al. |
| 8,886,337 B2 | 11/2014 | Bennett et al. |
| 8,965,516 B2 | 2/2015 | Bennett et al. |
| 9,072,897 B2 | 7/2015 | Sachs et al. |
| 9,079,019 B2 | 7/2015 | Crosby et al. |
| 9,108,053 B2 | 8/2015 | Crosby et al. |
| 9,320,847 B2 | 4/2016 | Rooney et al. |
| 9,561,364 B2 | 2/2017 | Bondhus |
| 9,861,811 B2 | 1/2018 | Crosby et al. |
| 9,950,159 B2 | 4/2018 | Beck et al. |
| 9,999,763 B2 | 6/2018 | Shiroff et al. |
| 10,016,603 B2 | 7/2018 | Sachs et al. |
| 10,195,419 B2 | 2/2019 | Shiroff et al. |
| 10,327,810 B2 | 6/2019 | Shiroff et al. |
| 10,471,268 B2 | 11/2019 | Crosby et al. |
| 2001/0053885 A1 | 12/2001 | Gielen et al. |
| 2002/0065543 A1 | 5/2002 | Gomperz et al. |
| 2002/0068960 A1* | 6/2002 | Saberski ............ A61N 1/36007 607/46 |
| 2002/0099419 A1 | 7/2002 | Cohen et al. |
| 2002/0115945 A1 | 8/2002 | Herman et al. |
| 2002/0147485 A1 | 10/2002 | Mamo et al. |
| 2002/0156513 A1 | 10/2002 | Borkan |
| 2002/0161415 A1 | 10/2002 | Cohen et al. |
| 2002/0183765 A1 | 12/2002 | Adams |
| 2003/0100933 A1 | 5/2003 | Ayal et al. |
| 2003/0120323 A1 | 6/2003 | Meadows et al. |
| 2003/0120328 A1 | 6/2003 | Jenkins et al. |
| 2003/0135120 A1 | 7/2003 | Parks et al. |
| 2003/0199938 A1 | 10/2003 | Smits et al. |
| 2004/0030360 A1 | 2/2004 | Eini et al. |
| 2004/0097986 A1 | 5/2004 | Adams |
| 2004/0111118 A1 | 6/2004 | Hill et al. |
| 2004/0122482 A1 | 6/2004 | Tung et al. |
| 2004/0147969 A1 | 7/2004 | Mann et al. |
| 2004/0167580 A1 | 8/2004 | Mann et al. |
| 2004/0214790 A1 | 10/2004 | Borgens |
| 2004/0230281 A1 | 11/2004 | Heil et al. |
| 2004/0236383 A1 | 11/2004 | Yelizarov |
| 2005/0070971 A1 | 3/2005 | Fowler et al. |
| 2005/0075701 A1 | 4/2005 | Shafer |
| 2005/0080472 A1 | 4/2005 | Atkinson et al. |
| 2005/0107861 A1 | 5/2005 | Harris et al. |
| 2005/0119713 A1 | 6/2005 | Whitehurst et al. |
| 2005/0149154 A1 | 7/2005 | Cohen et al. |
| 2005/0154389 A1 | 7/2005 | Selover et al. |
| 2005/0165456 A1 | 7/2005 | Mann et al. |
| 2005/0177211 A1 | 8/2005 | Leung et al. |
| 2005/0240243 A1 | 10/2005 | Barolat et al. |
| 2005/0246006 A1 | 11/2005 | Daniels |
| 2005/0283204 A1 | 12/2005 | Buhlmann et al. |
| 2006/0004429 A1 | 1/2006 | Mrva et al. |
| 2006/0009810 A1 | 1/2006 | Mann et al. |
| 2006/0009827 A1 | 1/2006 | Kurth et al. |
| 2006/0032657 A1 | 2/2006 | Zarembo |
| 2006/0052856 A1 | 3/2006 | Kim et al. |
| 2006/0106416 A1 | 5/2006 | Raymond et al. |
| 2006/0111746 A1 | 5/2006 | Foreman et al. |
| 2006/0111754 A1 | 5/2006 | Rezai et al. |
| 2006/0155341 A1 | 7/2006 | Tehrani |
| 2006/0184222 A1 | 8/2006 | Camps et al. |
| 2006/0206166 A1 | 9/2006 | Weiner |
| 2006/0235484 A1 | 10/2006 | Jaax et al. |
| 2006/0241716 A1 | 10/2006 | Finch et al. |
| 2006/0259074 A1 | 11/2006 | Kelleher et al. |
| 2006/0293662 A1 | 12/2006 | Boyer et al. |
| 2007/0027501 A1 | 2/2007 | Jensen et al. |
| 2007/0049980 A1 | 3/2007 | Zielinski et al. |
| 2007/0060967 A1 | 3/2007 | Strother et al. |
| 2007/0073357 A1 | 3/2007 | Rooney et al. |
| 2007/0100377 A1 | 5/2007 | Armstrong et al. |
| 2007/0100391 A1 | 5/2007 | Armstrong |
| 2007/0100408 A1 | 5/2007 | Gerber |
| 2007/0100411 A1 | 5/2007 | Bonde |
| 2007/0123954 A1 | 5/2007 | Gielen et al. |
| 2007/0129780 A1 | 6/2007 | Whitehurst et al. |
| 2007/0135768 A1 | 6/2007 | Carlsen |
| 2007/0179557 A1 | 8/2007 | Maschino et al. |
| 2007/0208392 A1 | 9/2007 | Kuschner et al. |
| 2007/0232936 A1 | 10/2007 | Mann et al. |
| 2007/0239224 A1 | 10/2007 | Bennett et al. |
| 2007/0276453 A1 | 11/2007 | Hill et al. |
| 2008/0026981 A1 | 1/2008 | Muhrer et al. |
| 2008/0103573 A1 | 5/2008 | Gerber |
| 2008/0103579 A1 | 5/2008 | Gerber |
| 2008/0132961 A1 | 6/2008 | Jaax et al. |
| 2008/0132969 A1 | 6/2008 | Bennett et al. |
| 2008/0147156 A1* | 6/2008 | Imran .................. A61N 1/0553 607/117 |
| 2008/0167698 A1 | 7/2008 | Kim et al. |
| 2008/0177351 A1 | 7/2008 | Fang et al. |
| 2008/0183221 A1 | 7/2008 | Burdulis |
| 2008/0183257 A1 | 7/2008 | Imran et al. |
| 2008/0200972 A1 | 8/2008 | Rittman et al. |
| 2008/0228241 A1 | 9/2008 | Sachs |
| 2008/0234791 A1 | 9/2008 | Arle et al. |
| 2008/0269716 A1 | 10/2008 | Bonde et al. |
| 2008/0269812 A1 | 10/2008 | Gerber et al. |
| 2009/0005833 A1 | 1/2009 | Cameron et al. |
| 2009/0018576 A1 | 1/2009 | Binmoeller |
| 2009/0020764 A1 | 1/2009 | Anderson et al. |
| 2009/0105700 A1 | 4/2009 | Anderson |
| 2009/0112263 A1 | 4/2009 | Pool et al. |
| 2009/0192567 A1 | 7/2009 | Armstrong et al. |
| 2009/0210041 A1 | 8/2009 | Kim et al. |
| 2009/0248095 A1 | 10/2009 | Schleicher et al. |
| 2009/0254095 A1 | 10/2009 | Levine et al. |
| 2009/0259280 A1 | 10/2009 | Wilkin et al. |
| 2009/0299201 A1 | 12/2009 | Gunderson |
| 2009/0326613 A1 | 12/2009 | Knoblich |
| 2010/0030227 A1 | 2/2010 | Kast et al. |
| 2010/0036280 A1 | 2/2010 | Ballegaard et al. |
| 2010/0036454 A1 | 2/2010 | Bennett et al. |
| 2010/0082086 A1 | 4/2010 | Zhu |
| 2010/0114206 A1 | 5/2010 | Kaemmerer et al. |
| 2010/0137938 A1 | 6/2010 | Kishawi et al. |
| 2010/0152808 A1 | 6/2010 | Boggs, II |
| 2010/0152809 A1 | 6/2010 | Boggs, II |
| 2010/0174240 A1 | 7/2010 | Wells et al. |
| 2010/0174326 A1 | 7/2010 | Selover et al. |
| 2010/0179562 A1 | 7/2010 | Linker et al. |
| 2010/0185161 A1 | 7/2010 | Pellegrino et al. |
| 2010/0211149 A1 | 8/2010 | Morgan et al. |
| 2010/0249875 A1 | 9/2010 | Kishawi et al. |
| 2010/0280576 A1 | 11/2010 | Gerber et al. |
| 2010/0292769 A1 | 11/2010 | Brounstein et al. |
| 2010/0331883 A1 | 12/2010 | Schmitz et al. |
| 2011/0004269 A1 | 1/2011 | Strother et al. |
| 2011/0021943 A1 | 1/2011 | Lacour et al. |
| 2011/0022114 A1 | 1/2011 | Navarro |
| 2011/0022123 A1 | 1/2011 | Stancer et al. |
| 2011/0054565 A1 | 3/2011 | Wacnik et al. |
| 2011/0106207 A1 | 5/2011 | Cauller et al. |
| 2011/0160538 A1 | 6/2011 | Ravikumar et al. |
| 2011/0190786 A1 | 8/2011 | Gerber et al. |
| 2011/0202112 A1* | 8/2011 | Ruais .................. A61B 5/0538 607/60 |
| 2011/0224665 A1 | 9/2011 | Crosby |
| 2011/0224682 A1 | 9/2011 | Westlund et al. |
| 2011/0251662 A1 | 10/2011 | Griswold et al. |
| 2011/0257660 A1 | 10/2011 | Jones et al. |
| 2011/0270340 A1 | 11/2011 | Pellegrini et al. |
| 2012/0035953 A1 | 2/2012 | Armstrong |

(56) References Cited

U.S. PATENT DOCUMENTS

| | | |
|---|---|---|
| 2012/0089153 A1 | 4/2012 | Christopherson et al. |
| 2012/0116477 A1 | 5/2012 | Crowe et al. |
| 2012/0192874 A1 | 8/2012 | Bolea et al. |
| 2012/0215218 A1 | 8/2012 | Lipani |
| 2012/0283800 A1 | 11/2012 | Perryman et al. |
| 2012/0290055 A1 | 11/2012 | Boggs, II |
| 2012/0310140 A1 | 12/2012 | Kramer et al. |
| 2012/0310301 A1 | 12/2012 | Bennett et al. |
| 2012/0310302 A1 | 12/2012 | Bennett et al. |
| 2012/0310314 A1 | 12/2012 | Bennett et al. |
| 2012/0323253 A1 | 12/2012 | Garai et al. |
| 2013/0023974 A1 | 1/2013 | Amrani |
| 2013/0053926 A1 | 2/2013 | Ordonez |
| 2013/0096641 A1 | 4/2013 | Strother et al. |
| 2013/0131766 A1 | 5/2013 | Crosby et al. |
| 2013/0155117 A1 | 6/2013 | Bang |
| 2013/0197607 A1 | 8/2013 | Wilder et al. |
| 2013/0197615 A1 | 8/2013 | Rundle et al. |
| 2013/0211487 A1 | 8/2013 | Fang et al. |
| 2013/0218247 A1 | 8/2013 | Sachs |
| 2013/0238066 A1 | 9/2013 | Boggs et al. |
| 2013/0245715 A1 | 9/2013 | Peterson |
| 2013/0253605 A1* | 9/2013 | Bennett ............ A61N 1/36021 607/46 |
| 2013/0261696 A1 | 10/2013 | Thacker et al. |
| 2013/0296966 A1 | 11/2013 | Wongsarnpigoon et al. |
| 2013/0310901 A1 | 11/2013 | Perryman et al. |
| 2013/0338730 A1 | 12/2013 | Shiroff et al. |
| 2014/0031837 A1 | 1/2014 | Perryman et al. |
| 2014/0039574 A1 | 2/2014 | Bradley |
| 2014/0046398 A1 | 2/2014 | Sachs et al. |
| 2014/0058476 A1 | 2/2014 | Crosby et al. |
| 2014/0114385 A1 | 4/2014 | Nijhuis et al. |
| 2014/0288616 A1 | 9/2014 | Rawat et al. |
| 2014/0350653 A1 | 11/2014 | Shiroff et al. |
| 2015/0105840 A1 | 4/2015 | Boggs, II |
| 2015/0306405 A1 | 10/2015 | Sachs et al. |
| 2015/0374992 A1 | 12/2015 | Crosby et al. |
| 2016/0045746 A1 | 2/2016 | Jiang et al. |
| 2016/0045747 A1 | 2/2016 | Jiang et al. |
| 2016/0067476 A1 | 3/2016 | Rawat et al. |
| 2016/0106994 A1 | 4/2016 | Crosby et al. |
| 2016/0213927 A1 | 7/2016 | McGee et al. |
| 2016/0310732 A1 | 10/2016 | Beck et al. |
| 2017/0100408 A1 | 4/2017 | Bertolini et al. |
| 2018/0008311 A1 | 1/2018 | Shiroff |
| 2019/0328423 A1 | 10/2019 | Shiroff et al. |
| 2020/0203858 A1 | 6/2020 | Youtsey |

FOREIGN PATENT DOCUMENTS

| | | |
|---|---|---|
| CN | 101678203 | 3/2010 |
| EP | 0 587 269 A2 | 3/1994 |
| EP | 0 587 269 B1 | 12/1998 |
| EP | 1 053 762 B1 | 11/2000 |
| EP | 1 255 583 A1 | 11/2002 |
| EP | 1053762 B1 | 8/2005 |
| EP | 1255583 B1 | 12/2007 |
| EP | 2 125 100 A1 | 12/2009 |
| EP | 2 273 931 A1 | 1/2011 |
| WO | WO-01/58520 A1 | 8/2001 |
| WO | WO-2004/066820 A2 | 8/2004 |
| WO | WO-2006/091611 A1 | 8/2006 |
| WO | WO-2006/133445 A2 | 12/2006 |
| WO | WO-2006/135791 A2 | 12/2006 |
| WO | WO-2007/051146 A1 | 5/2007 |
| WO | WO-2007/138598 A2 | 12/2007 |
| WO | WO-2008/048471 A2 | 4/2008 |
| WO | WO-2008/070807 A2 | 6/2008 |
| WO | WO-2008/094952 A2 | 8/2008 |
| WO | WO-2008/112178 A1 | 9/2008 |
| WO | WO-2009/020764 A1 | 2/2009 |
| WO | WO-2009/134475 A1 | 11/2009 |
| WO | WO-2010/062600 A2 | 6/2010 |
| WO | WO-2010/062622 A2 | 6/2010 |
| WO | WO-2011/079866 A1 | 7/2011 |
| WO | WO-2011/112773 A1 | 9/2011 |
| WO | WO-2012/057916 A1 | 5/2012 |
| WO | WO-2012/091747 A1 | 7/2012 |
| WO | WO-2013/016268 A1 | 1/2013 |
| WO | WO-2013/019853 A1 | 2/2013 |
| WO | WO-2013/036630 A1 | 3/2013 |
| WO | WO-2013/096260 A1 | 6/2013 |
| WO | WO-2013138786 A1 | 9/2013 |
| WO | WO-2013/155117 A1 | 10/2013 |
| WO | WO-2014/099423 A1 | 6/2014 |
| WO | WO-2015/059570 A1 | 4/2015 |
| WO | WO-2015/187426 A1 | 12/2015 |
| WO | WO-2018/007914 A1 | 1/2018 |

OTHER PUBLICATIONS

Baker et al., "Clinical Uses of Neuromuscular Electrical Stimulation," NeuroMuscular Electrical Stimulation—A Practical Guide, 4th ed. Rancho Los Amigos Research and Education Institute Inc., pp. 47-66 (2000).

Bhadra et al., "Peripheral nerve stimulation for restoration of motor function," Journal of Clinical Neurophysiology: Official Publication of the American Electroencephalographic Society, 14(5):378-33 (Sep. 1997).

Bogie et al., "Effects of regular use of neuromuscular electrical stimulation on tissue health," Journal of Rehabilitation Research and Development, 40(6):469-475 (2003) available at: http://www.ncbi.nlm.nih.gov/pubmed/15077659 (Accessed Jan. 18, 2011).

Bowman et al., "Effects of Waveform Parameters on Comfort during Transcutaneous Neuromuscular Electrical Stimulation," Annals of Biomedical Engineering, 13:59-74 (1985).

Bradford et al., "Surface Electrical Stimulation in the Treatment of Idiopathic Scoliosis: Preliminary Results in 30 Patients," Spine, 8(7):757-764 (1983).

Brazier et al., "A Comparison of the EQ-5D and SF-6D Across Seven Patient Groups," Health Economics, 13:873-884 (2004).

Coghlan et al., "Electrical muscle stimulation for deep stabilizing muscles in abdominal wall," Conference proceedings: . . . Annual International Conference of the IEEE Engineering in Medicine and Biology Society. IEEE Engineering in Medicine and Biology Society. Conference, pp. 2756-2759 (2008) available at: http://www.ncbi.nlm.nih.gov/pubmed/19163276.

Coghlan et al., "Neuromuscular electrical stimulation training results in enhanced activation of spinal stabilizing muscles during spinal loading and improvements in pain ratings," Conference proceedings: . . . Annual International Conference of the IEEE Engineering in Medicine and Biology Society. IEEE Engineering in Medicine and Biology Society. Conference, pp. 7622-7625 (2011) available at: http://www.ncbi.n1m.nih.gov/pubmed/22256103.

Crago et al., "The choice of pulse duration for chronic electrical stimulation via surface, nerve, and intramuscular electrodes," Annals of Biomedical Engineering, 2(3):252-264 (1974).

Criterion Inc., "NMES Treatment Protocols," 3 pages (accessed Jun. 7,2012) available at http://www.criterionmed.com/PDF/NMES%20Treatment%20Protocols.pdf.

Deckers, et al., Chronic Low Back Pain: Restoration of Dynamic Stability, Neuromodulation, 18:478-486 (2015).

Durham et al., "Surface Electrical Stimulation Versus Brace in Treatment of Idiopathic Scoliosis," Spine, 15(9):888-891 (1990).

Empi, "Low Back Syndrome/Chronic Low Back Pain," NMES Guidelines for Treatment, 2 pages (2003).

Extended European Search Report dated Jan. 7, 2013 in European Patent Appl. No. 12176863.

Extended European Search Report dated Mar. 5, 2015 in EP Patent Appl. Serial No. 14189412.1.

Ferreira et al., "Comparison of general exercise, motor control exercise and spinal manipulative therapy for chronic low back pain: A randomized trial," Pain, 131(1-2):31-37 (2007) available at: http://www.ncbi.nlm.nih.gov/pubmed/17250965.

(56) References Cited

OTHER PUBLICATIONS

Freeman, et al., The Role of the Lumbar Multifidus in Chronic Low Back Pain: A Review, American Academy of Physical Medicine and Rehabilitation, 2:142-146 (2010).
Friedman et al., "Electrical stimulation for scoliosis," American Family Physician, 25(4):155-160 (1982) available at: http://www.ncbi.nlm.nih.gov/pubmed/6978055 (Accessed Oct. 19, 2011).
Garmirian, et al., Discriminating Neurogenic from Myopathic Disease via Measurement of Muscle Anisotrophy, Muscle Nerve, 39(1):16-24 (2009) (Abstract only).
Gazelle et al., "Tumor Ablation with radio-frequency Energy," Radiology, (2000), 217(3):633-646.
Glaser et al., "Electrical Muscle Stimulation as an Adjunct to Exercise Therapy in the Treatment of Nonacute Low Back Pain: A Randomized Trial," The Journal of Pain, 2(5):295-300 (2001).
Gondin, et al., Electromyostimulation training effects on neural drive and muscle architecture, Med. Sci. Sports. Exerc., 37(8):1291-9 (2005).
Gorman et al., "The effect of stimulus parameters on the recruitment characteristics of direct nerve stimulation," IEEE Transactions on Bio-medical Engineering, 30(7):407-414 (1983).
Haemmerich et al., "Thermal Tumor Ablation: Devices, Clinical Applications and Future Directions," Int. J. Hyperthermia, (2005) 21(8):775-760 (Abstract).
Hagg et al., "The Clinical Importance of Changes in Outcome Scores After Treatment for Chronic Low Back Pain," Eur. Spine. J., 12:12-20 (2003).
Herbert et al., "Scoliosis Treatment in Children Using a Programmable, Totally Implantable Muscle Stimulator (ESI)," IEEE Transactions on Biomedical Engineering, 36(7):801 (Jul. 1989).
Hodges et al., "Response of the deep paraspinal muscles to cortical but not transmastoid stimulation is increased at a single lumbar level following intervertebral disc lesion," Progress in Motor Control Vi-Brazil. 36:2-3 (2007).
Hodges, et al., Intervertebral Stiffness of the Spine is Increased by Evoked Contraction of Transversus Abdominis and the Diaphragm: In Vivo Porcine Studies, Spine 28(23):2594-2601 (2003) (Abstract only).
Hodges, Is There a Role for Transversus Abdominis in Lumbo-Pelvis Stability? Manual Therapy, 4(2):74-86 (1999).
Holm, et al., Sensorimotor Control of the Spine, J. Electromyogr. Kinesiol. 12(3):219-34 (2002) (Abstract only).
Hortobagyi et al., "Neural adaptations to electrical stimulation strength training," European Journal of Applied Physiology, 2439-2449 (2011) available at: http://www.ncbi.nlm.nih.gov/pubmed/21643920 (Accessed Jul. 19, 2011).
Informal Response to Written Opinion dated Jan. 17, 2012 in Int'l PCT Patent Appl. Serial No. PCT/US2011/027834.
International Search Report & Written Opinion dated Jan. 19, 2016 in Int'l PCT Patent Appl. Serial No. PCT/IB2015/055926.
International Search Report & Written Opinion dated Mar. 19, 2015 in Int'l PCT Patent Appl. Serial No. PCT/IB2014/002920.
International Search Report & Written Opinion dated Apr. 5, 2013 in Int'l PCT Patent Appl. Serial No. PCT/US2012/070259.
International Search Report & Written Opinion dated Sep. 28, 2017 in Int'l PCT Patent Appl. Serial No. PCT/IB2017/053945.
International Search Report & Written Opinion dated Oct. 20, 2017 in Int'l PCT Patent Appl. Serial No. PCT/IB2017/053946.
International Search Report & Written Opinion dated Jun. 25, 2008 in Int'l PCT Patent Appl. Serial No. PCT/US08/03126.
International Search Report and Written Opinion dated Jan. 26, 2016 in Int'l PCT Patent Appl. Serial No. PCT/IB2015/057838.
International Search Report and Written Opinion dated Oct. 16, 2015 in Int'l PCT Patent Appl. Serial No. PCT/US2015/032732.
International Search Report dated Oct. 19, 2011 in Int'l PCT Patent Appl. Serial No. PCT/US2011/027934.
Keller, et al., Muscular Contributions to Dynamic Dorsoventral Lumber Spine Stiffness, Eur. Spine J., 16(2):245-54 (2007).
Kiesel et al., Measurement of lumbar multifidus muscle contraction with rehabilitative ultrasound imaging, Manual Therapy, 12(2):161-166 (2007) available at: ttp://www.ncbi.nlm.nih.gov/pubmed/16973400.
Lauridsen et al., "Responsiveness and Minimal Clinically Important Difference for Pain and Disability Instruments in Low Back Pain Patients," BMC Musculoskeletal Disorders, 7(82):16 pages (2006).
Lieber, Richard, Comparison between animal and human studies of skeletal muscle adaptation to chronic stimulation, Clinical Orthopaedics and related research, No. 233, pp. 19-24 (1988).
Lieber, Richard, Skeletal muscle adaptability. II: Muscle properties following spinal-cord injury, Developmental medicine and Child Neurology 28(4):533-42 (1986).
Lieber, Richard, Skeletal muscle adaptability. III: Muscle properties following chronic electrical stimulation, Developmental medicine and Child Neurology 28(5):662-70 (1986).
Medtronic Extension Passer 3555 Accessory Kit—Technical Instructions, 2 pages (2001).
Medtronic Interstim Therapy 3093 & 3889—Implant Manual, 38 pages (2010).
Medtronic Model 3464 Receiver/Extension Internalization Manual, SE-4 for Spinal Cord Stimulation (SCS), 7 pages (1986).
Medtronic Tunneling Rod Accessory Kit 8590-41—Technical Manual, 9 pages (No date available).
MicroProbes for Life Science, Nerve Cuff Electrodes, 2018, available at https://microprobes.com/products/peripheral-electrodes/nerve-cuff, accessed Mar. 5, 2018.
Miyatani, et al., Validity of Estimating Limb Muscle vol. By Bioelectrical Impedance, J. Appl. Physiol., 91:386-394 (2001).
Mortimer et al., "Intramuscular electrical stimulation: tissue damage," Annals of Biomedical Engineering, 8(3):235-244 (1980).
Mortimer et al., "Peripheral Nerve and Muscle Stimulation. In: Horch KW, Dhillon G, eds," Neuroprosthetics: Theory and Practice (Series on Bioengineering & Biomedical Engineering—vol. (2), World Scientific Publishing Company, pp. 1-48 (2005).
Nachemson et al., "Effectiveness of Treatment with a Brace in Girls Who Have Adolescent Idiopathic Scoliosis," The Journal of Bone and Joint Surgery, 77-A(6):815-819 (Jun. 1995).
Oaao Bock, "ActiGait Implantable Drop Foot Stimulator," Surgeon Manual, 28 pages (2006).
O'Donnell et al., "Electrical Stimulation in the Treatment of Idiopathic Scoliosis," Clinical Orthopaedics and Related Research, No. 229:107-112 (Apr. 1988).
Paicius et al., "Peripheral Nerve Field Stimulation for the Treatment of Chronic Low Back Pain: Preliminary Results of Long-Term Follow-up: A Case Series," Neuromodulation, 10(3):279-290 (2007) available at: http://www.blackwell-synergy.com/doi/abs/10.1111/.1525-1403.2007.00116.x.
Panjabi, Manohar, "A hypothesis of chronic back pain: ligament subfailure injuries lead to muscle control dysfunction," European spine journal: official publication of the European Spine Society, the European Spinal Deformity Society, and the European Section of the Cervical Spine Research Society 15, No. 5 (May 2006): 668-676. http://www.ncbi.nlm.nih.gov/pubmed/16047209.
Panjabi, Manohar, "The stabilizing system of the spine. Part 1. Function, dysfunction, adaptation, and enhancement," Journal of Spinal Disorders, 5(4)383-389 (Dec. 1992), Discussion 397. http://www.ncbi.nlm.nih.gov/pubmed/1490034.
Panjabi, Manohar, "The stabilizing system of the spine. Part II. Neutral zone and instability hypothesis," Journal of Spinal Disorders, 5(4):390-396 (Dec. 1992), Discussion 397. http://www.ncbi.nlm.nih.gov/pubmed/1490035.
Partial International Search Report dated Aug. 4, 2015 in Int'l PCT Patent App. Serial No. PCT/US2015/032732.
PCT International Search Report and Written Opinion dated Sep. 3, 2013 in related PCT Appl. No. PCT/US2013/045223.
PCT Written Opinion dated Aug. 23, 2013 in Int'l PCT Appl. Serial No. PCT/US2010/049148.
Peckham et al., "Functional electrical stimulation for neuromuscular applications," Annual review of Biomedical Engineering, 7:327-360 (2005) available at: http://www.ncbi.nlm.nih.gov/pubmed/16004574.

(56) References Cited

OTHER PUBLICATIONS

Peterson et al., "Long-term intramuscular electrical activation of the phrenic nerve: safety and reliability," IEEE Transactions on Biomedical Engineering, 41(12):1115-1126 (1994).
Poitras et al., "Evidence-informed management of chronic low back pain with transcutaneous electrical nerve stimulation, interferential current, electrical muscle stimulation, ultrasound, and thermotherapy," The Spine Journal 8:226-233 (2008).
Reed B., :The Physiology of Neuromuscular Electrical Stimulation, Pediatric Physical Therapy, 9(3):96-102 (1997) available at: http://journals.lww.com/pedpt/pages/artic1eviewer.aspx?year=1997&issue=00930&article=00002&type=abstract.
Rosatelli, et al., Three-dimensional study of the musculotendinous architecture of lumbar multifidus and its functional implications, Clinical Anatomy 21(6):539-44 (2008).
RS Medical, "RS-4M Muscle Stimulator," available at http://www.rsmedical.com/documents/fact_sheet_RS4m.pdf (last visited Jul. 19, 2012).
Russo, M.D., et al., Muscle Control and Non-Specific Chronic Low Back Pain, Neuromodulation: Technology at the Neural Interface, 21:1-9 (2017).
Rutkove, "Electrical Impedance Myography: Background, Current State, and Future Directions," Muscle Nerve, 40(6):936-946 (2009).
Schwartz et al., "Therapeutic Electrical Stimulation of the Hypoglossal Nerve in Obstructive Sleep Apnea," Arch Otolaryngal Head Neck Surg., 127:1216-1223 (2001).
Sheffler et al., "Neuromuscular Electrical Stimulation in Neurorehabilitation," Muscle Nerve, 35: 562-590 (2007).
Sippl, Charles J., "Computer Dictionary: Third Edition," pp. 2257 and 340 (1984).
Sluijter, "Radiofrequency Ablation in the Management of Spinal Pain," C212, (2006), IV(1):10-15.
Solomonow et al., "The Ligamento-Muscular Stabilizing System of the Spine," Spine, (1998), 23(23):2552-2562.
Spinal Fusion Guidelines, MD Guidelines, 2009. www.mdguidelines.com/spinal-fusion.
Stokes, et al., "Surface EMG Electrodes Do Not Accurately Record from Lumbar Multifidus Muscles," Clin. Biomech, (2003), 18(1):9-13 (Abstract Only).
Unit III—The Spine, "Motions of the Spine," available at https://courses.vcu.edu/DANC291-003/unit_3.htm, accessed Mar. 5, 2018.
Van Dieen, et al., "Trunk Muscle Recruitment Patterns," Spine, (2003), 28(8):834-841 (Abstract Only).
Van et al., "The use of real-time ultrasound imaging for biofeedback of lumbar multifidus muscle contraction in healthy subjects," The Journal of Orthopaedic and Sports Physical Therapy, 36(12):920925 (2006) available at: http://www.ncbi.n1m.nih.gov/pubmed/17193869.
Van Zundert et al., "Radiofrequency treatment for chronic pain syndromes," CPD Anaesthesis, 6(1):13-17 (2004).
Verrills et al., "Peripheral Nerve Stimulation: A Treatment for Chronic Low Back Pain and Failed Back Surgery Syndrome?," Neuromodulation: Technology at the Neural Interface, (2009), 12(1):68-75.
Vrbova et al., Application of Muscle/Nerve Stimulation in Health and Disease, Springer Verlag (2008) available at: http://books.google.com/books?hl=en&1r=&id=jb8fDGxkbqEC&oi=fnd&pg=PAI&dq=Application of Muscle/Nerve Stimulation in Health and Disease&ots=CMV5rXiDQD&sig=Wg8u1YOC4PgvVDzcjdwBub5U2To (Accessed Jun. 2, 2011).
Wallwork et al., "The effect of chronic low back pain on size and contraction of the lumbar multifidus muscle," Manual Therapy, 14(5):496-500 (2009) available at: http://www.ncbi.nlm.nih.gov/pubmed/19027343.
Ward et al., "Architectural analysis and intraoperative measurements demonstrate the unique design of the multifidus for lumbar spine stability," J. Bone Joint Surg. [Am.] 91:176-185, PMC2663324 (2009).

Wikipedia, "Anterior superior iliac spine," Updated Feb. 12, 2018, available at https://en.wikipedia.org/wiki/Anterior_superior_iliac_spine.
Wikipedia, "Blunt Dissection," Updated Feb. 14, 2018, available at https://en.wikipedia.org/wiki/Blunt_dissection.
Wikipedia, "Cavernous nerves," Updated Feb. 26, 2018, available at https://en.wikipedia.org/wiki/Cavernous_nerves.
Wikipedia, "Dorsal ramus of spinal nerve," Updated Feb. 12, 2018, available at https://en.wikipedia.org/wiki/Dorsal_ramus_of_spinal_nerve.
Wikipedia, "Interference Fit," http://en.wikipedia.org/wiki/Interference_fit, accessed Dec. 4, 2014.
Wikipedia, "Time-division multiplexing," https://en.wikipedia.org/wiki/Time-division_multiplexing (accessed Nov. 12, 2015).
Wikipedia, "Ventral ramus of spinal nerve," Updated Feb 12, 2018, available at https://en.wikipedia.org/wiki/Ventral_ramus_of_spinal_nerve.
Wright et al., "Morphologic and histochemical characteristics of skeletal muscle after long-term intramuscular electrical stimulation," Spine, 17(7):767-770 (1992) available at: http://www.ncbi.nlm.nih.gov/pubmed/1502640 (Accessed Aug. 2, 2011).
Written Opinion dated Feb. 3, 2014 in Int'l PCT Patent Appl. Serial No. PCT/US2012/070259.
Written Opinion dated Nov. 16, 2011 in Int'l PCT Patent Appl. Serial No. PCT/US2011/027934.
Costa et al., Motor Control Exercise for Chronic Low Back Pain: A Randomized Placebo-Controlled Trial, Physical Therapy, 89(12):1275-1286 (2009).
Dworkin et al., *Interpreting the Clinical Importance of Treatment Outcomes in Chronic Pain Clinical Trials:Immpact Recommendations*, The Journal of Pain, 9(2):105-121 (2008).
Extended European Search Report dated Feb. 24, 2020 in EP Patent Appl. Serial No. 08726632.6 (0230).
Extended European Search Report dated Sep. 30, 2019 in EP Patent Appl. Serial No. 19173003.5 (0840).
Ghamkhar, et al., *Application of rehabilitative ultrasound in the assessment of low back pain: a literature review*, Journal of Bodywork & Movement Therapies, 15(4):465-477 (2011).
Gondin, et al., "Electromyostimulation Training Effects on Neural Drive and Muscle Architecture." Med. Sci. Sports Exerc., 37(8):1291-1299, (2005).
Hauggaard et al., "Specific spinal stabilisation exercises in patients with low back pain—a systematic review." Physical Therapy Reviews, 12(3):233-248 (2007).
Hebert et al., *The Relationship of Transversus Abdominis and Lumbar Multifidus Activation and Prognostic Factors for Clinical Success With a Stabilization Exercise Program: A Cross-Sectional Study*, Arch. Phys. Med. Rehabil., 91:78-85 (2010).
Hides et al., *Long-Term Effects of Specific Stabilizing Exercises for First-Episode Low Back Pain*, Spine, 26(11):E243-248 (2001).
Informal Response to Written Opinion dated Jan. 17, 2012 in Int'l PCT Patent Appl. No. PCT/US2011/027934.
International Search Report & Written Opinion dated Oct. 17, 2012 in Int'l PCT Patent Appl. No. PCT/US12/49148 (0510).
International Search Report & Written Opinion dated Oct. 19, 2011 in Int'l PCT Patent Appl. No. PCT/US11/27834, 12 pages (0410).
McIntosh, et al., Low back pain (chronic), Clin. Evid., 10:1-28(2008).
Medtronic, Kinetra, Soletra, and Itrel II, 8870, Neurostimulators for Deep Brain Stimulation (DBS), Software Application Card, Programming Guide for Software A, Dec. 1, 2003, Published 2005, Retrieved from the Internet: URL:http://www.boala-parkinson.ro/Carti%20tehnice/dbs-prog8870-gd.pdf [retrieved Aug. 23, 2018].
Ostelo et al., Interpreting Change Scores for Pain and Functional Status in Low Back Pain: Towards International Consensus Regarding Minimal Important Change, Spine, 33(1):90-94 (2008).
Soer et al., *Clinimetric properties of the EuroQol-50 in patients with chronic low backpain*, The Spine Journal, 12:1035-1039 (2012).
Van Buyten et al., *Neuromuscular Reactivation—A New Therapy for Patients with Chronic Low Back Pain (CLBP): Results of a European Multicenter Feasibility Study*, Neuromodulation, 16:e176 (2013).
U.S. Appl. No. 12/075,174 / U.S. Pat. No. 8,428,728, filed Mar. 10, 2008 / Apr. 23, 2013.

(56) References Cited

OTHER PUBLICATIONS

U.S. Appl. No. 13/045,421 / U.S. Pat. No. 9,248,278, filed Mar. 10, 2011 / Feb. 2, 2016.
U.S. Appl. No. 13/045,435, filed Mar. 10, 2011.
U.S. Appl. No. 13/564,584 / U.S. Pat. No. 9,079,019, filed Aug. 1, 2012 / Jul. 14, 2015.
U.S. Appl. No. 13/718,806 / U.S. Pat. No. 9,108,053, filed Dec. 18, 2012 / Aug. 18, 2015.
U.S. Appl. No. 13/797,100 / U.S. Pat. No. 9,999,763, filed Mar. 12, 2013 / Jun. 19, 2018.
U.S. Appl. No. 13/858,809 / U.S. Pat. No. 8,606,358, filed Apr. 8, 2013 / Dec. 10, 2013.
U.S. Appl. No. 14/061,614 / U.S. Pat. No. 9,072,897, filed Oct. 23, 2013 / Jul. 7, 2015.
U.S. Appl. No. 14/295,153 / U.S. Pat. No. 9,186,501, filed Jun. 3, 2014 / Nov. 17, 2015.
U.S. Appl. No. 14/453,423 / U.S. Pat. No. 10,195,419, filed Aug. 6, 2014 / Feb. 5, 2019.
U.S. Appl. No. 14/792,430 / U.S. Pat. No. 9,474,906, filed Jul. 6, 2015 / Oct. 25, 2016.
U.S. Appl. No. 14/849,478 / U.S. Pat. No. 9,861,811, filed Sep. 9, 2015 / Jan. 9, 2018.
U.S. Appl. No. 14/882,087, filed Oct. 31, 2015.
U.S. Appl. No. 14/939,955 / U.S. Pat. No. 9,981,122, filed Nov. 12, 2015 / May 29, 2018.
U.S. Appl. No. 15/202,435 / U.S. Pat. No. 9,950,159, filed Jul. 5, 2016 / Apr. 24, 2018.
U.S. Appl. No. 15/202,485, filed Jul. 5, 2016.
U.S. Appl. No. 15/299,399 / U.S. Pat. No. 10,016,603, filed Oct. 20, 2016 / Jul. 10, 2018.
U.S. Appl. No. 15/853,543, filed Dec. 22, 2017.
U.S. Appl. No. 15/944,730, filed Apr. 3, 2018.
U.S. Appl. No. 15/948,945, filed Apr. 9, 2018.

* cited by examiner

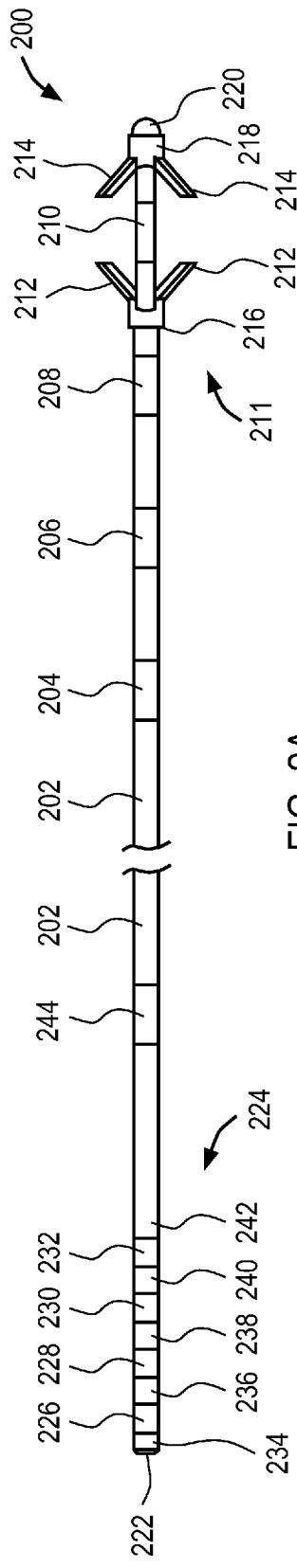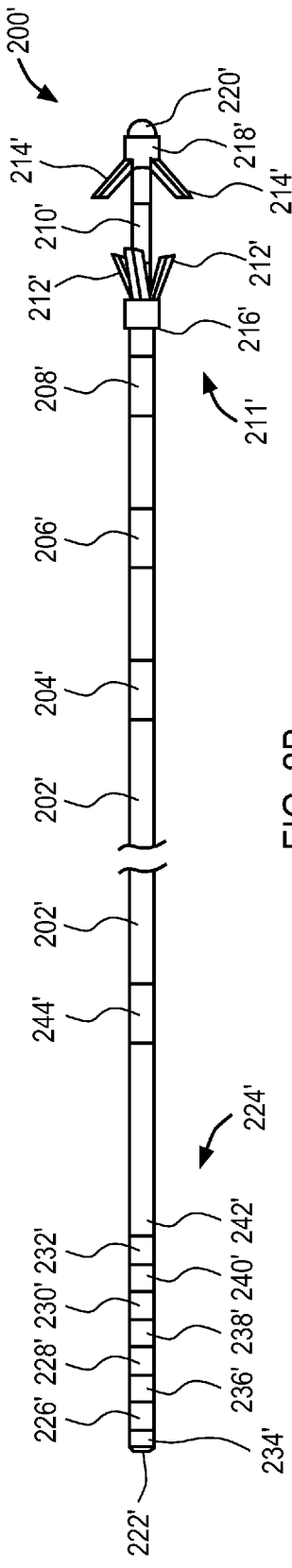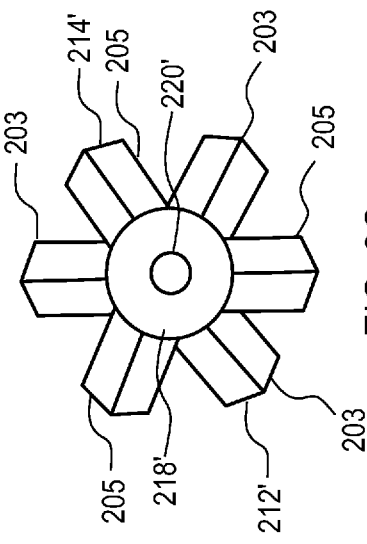

SYSTEMS AND METHODS FOR ENHANCING FUNCTION OF SPINE STABILIZATION MUSCLES ASSOCIATED WITH A SPINE SURGERY INTERVENTION

CROSS-REFERENCE TO RELATED APPLICATIONS

This application is a continuation-in-part of U.S. patent application Ser. No. 15/944,730, filed Apr. 3, 2018, which is a continuation of U.S. patent application Ser. No. 15/299,399, filed Oct. 20, 2016, now U.S. Pat. No. 10,016,603, which is a continuation of U.S. patent application Ser. No. 14/792,430, filed Jul. 6, 2015, now U.S. Pat. No. 9,474,906, which is a continuation of U.S. patent application Ser. No. 14/061,614, filed Oct. 23, 2013, now U.S. Pat. No. 9,072,897, which is a continuation-in-part of application of U.S. patent application Ser. No. 13/858,809, filed Apr. 8, 2013, now U.S. Pat. No. 8,606,358, which is a continuation of U.S. patent application Ser. No. 12/075,174, filed Mar. 10, 2008, now U.S. Pat. No. 8,428,728, which claims the benefit of priority of U.S. Provisional Application Ser. No. 60/905,979, filed Mar. 9, 2007, the entire contents of each of which are incorporated herein by reference.

FIELD OF THE INVENTION

This application generally relates to systems and methods for neuromuscular electrical stimulation, including stimulation of spine stabilization muscles to enhance function prior to, during, or after a planned spine surgery intervention.

BACKGROUND OF THE INVENTION

The human back is a complicated structure including bones, muscles, ligaments, tendons, nerves and other structures. The spinal column has interleaved vertebral bodies and intervertebral discs and permits motion in several planes including flexion-extension, lateral bending, axial rotation, longitudinal axial distraction-compression, anterior-posterior sagittal translation, and left-right horizontal translation. The spine provides connection points for a complex collection of muscles that are subject to both voluntary and involuntary control.

Back pain in the lower or lumbar region of the back is common. In many cases, the cause of back pain is unknown. It is believed that some cases of back pain are caused by abnormal mechanics of the spinal column. Degenerative changes, injury of the ligaments, acute trauma, or repetitive microtrauma may lead to back pain via inflammation, biochemical and nutritional changes, immunological factors, changes in the structure or material of the endplates or discs, and pathology of neural structures.

The spinal stabilization system may be conceptualized to include three subsystems: 1) the spinal column, which provides intrinsic mechanical stability; 2) the spinal muscles, which surround the spinal column and provide dynamic stability; and 3) the neuromotor control unit, which evaluates and determines requirements for stability via a coordinated muscle response. In patients with a functional stabilization system, these three subsystems work together to provide mechanical stability. In many cases, low back pain results from dysfunction of these subsystems. A summary of the theory and mechanism of action of this cause of back pain can be found in Mark Russo, M. D., et al., *Muscle Control and Non-specific Chronic Low Back Pain*, Neuromodulation: Technology at the Neural Interface 21: 1-9 (2017) (also available at: https://doi.org/10.1111/ner.12738).

The spinal column consists of vertebrae and ligaments, e.g. spinal ligaments, disc annulus, and facet capsules. There has been an abundance of in-vitro work in explanted cadaver spines and models evaluating the relative contribution of various spinal column structures to stability, and how compromise of a specific column structure will lead to changes in the range of motion of spinal motion segments.

The spinal column also has a transducer function, to generate signals describing spinal posture, motions, and loads via mechanoreceptors present in the muscles, tendons, ligaments, facet capsules, disc annulus, and other connective tissues. This function is often referred to as proprioception. These mechanoreceptors provide information to the neuromuscular control unit, which generates muscle response patterns to activate and coordinate the spinal muscles to provide muscle mechanical stability. Ligament injury, fatigue, and viscoelastic creep may corrupt signal transduction. If spinal column structure is compromised, due to injury, degeneration, or viscoelastic creep, then muscular stability must be increased to compensate and maintain stability.

Muscles provide mechanical stability to the spinal column. The vertebrae, and in particular the vertebral bodies, support compressive loads, e.g., the weight of the upper body; whereas, the muscles stabilize the vertebral column and prevent buckling much like guy wires are used to provide stability to a tall radio antenna.

Under normal circumstances, the mechanoreceptors exchange signals with the neuromuscular control unit for interpretation and action. The neuromuscular control unit generates signals that produce a dynamic muscle response pattern based upon several factors, including the need for spinal stability, postural control, balance, and stress reduction on various spinal components.

It is believed that in some patients with back pain, the spinal stabilization system is dysfunctional. With soft tissue injury, mechanoreceptors may produce corrupted signals about vertebral position, motion, or loads, leading to an inappropriate muscle response. In addition, muscles themselves may be injured, fatigued, atrophied, or lose their strength, thus aggravating dysfunction of the spinal stabilization system. Conversely, muscles can disrupt the spinal stabilization system by going into spasm, contracting when they should remain inactive, or contracting out of sequence with other muscles. As muscles participate in the feedback loop via mechanoreceptors in the form of muscle spindles and golgi tendon organs, muscle dysfunction may further compromise normal muscle activation patterns via the feedback loops.

Trunk muscles may be categorized into local and global muscles. The local muscle system includes deep muscles, and portions of some muscles that have their origin or insertion on the vertebrae. These local muscles control the stiffness and intervertebral relationship of the spinal segments. They provide an efficient mechanism to fine-tune the control of intervertebral motion. The lumbar multifidus, and in particular the deep fascicles of the multifidus, with its vertebra-to-vertebra attachments is an example of a muscle of the local system. Another example is the transverse abdominis, with its direct attachments to the lumbar vertebrae through the thoracolumbar fascia.

The multifidus is the largest and most medial of the lumbar back muscles. It has a repeating series of fascicles which stem from the laminae and spinous processes of the vertebrae, and exhibit a constant pattern of attachments caudally. These fascicles are arranged in five overlapping groups such that each of the five lumbar vertebrae gives rise to one of these groups. At each segmental level, a fascicle arises from the base and caudolateral edge of the spinous process, and several fascicles arise, by way of a common tendon, from the caudal tip of the spinous process. Although confluent with one another at their origin, the fascicles in each group diverge caudally and laterally to assume separate attachments to the mamillary processes, the iliac crest, and the sacrum. Some of the deep fibers of the fascicles that attach to the mamillary processes attach to the capsules of the facet joints next to the mamillary processes. The fascicles arriving from the spinous process of a given vertebra are innervated by the medial branch of the dorsal ramus nerve that issues from below that vertebra.

The global muscle system encompasses the large, superficial muscles of the trunk that cross multiple motion segments, and do not have direct attachment to the vertebrae. These muscles are the torque generators for spinal motion, and control spinal orientation, balance the external loads applied to the trunk, and transfer load from the thorax to the pelvis. Global muscles include the obliquus internus abdominis, the obliquus externus abdominis, the rectus abdominis, the lateral fibers of the quadratus lumborum, and portions of the erector spinae.

Normally, load transmission via the spinal column is painless. Over time, dysfunction of the spinal stabilization system is believed to lead to instability, resulting in overloading of structures when the spine moves beyond its neutral zone leading to pain. The neutral zone is a range of intervertebral motion, measured from a neutral position, within which the spinal motion is produced with a minimal internal resistance. High loads can lead to inflammation, disc degeneration, facet joint degeneration, and muscle fatigue. Since the disc endplates and annulus have a rich nerve supply, it is believed that abnormally high loads on the disc may be a cause of pain. Load transmission to the facets also may change with degenerative disc disease as the disc is compressed, leading to facet arthritis and facet pain.

For patients believed to have back pain due to instability, clinicians may offer treatments intended to reduce intervertebral motion. Common methods of attempting to improve muscle strength and control include core abdominal exercises, use of a stability ball, and Pilates. Spinal fusion is a standard surgical treatment for chronic back pain, particularly if there is demonstrated instability from abnormal relative motion of the vertebrae. Following fusion, motion is reduced across the vertebral motion segment. Dynamic stabilization implants are intended to reduce abnormal motion and load transmission of a spinal motion segment, without fusion. Categories of dynamic stabilizers include interspinous process devices, interspinous ligament devices, and pedicle screw-based structures. Total disc replacement and artificial nucleus prostheses also aim to improve spine stability and load transmission while preserving motion.

There are a number of problems associated with current implants that aim to restore spine stabilization. First, it is difficult to achieve uniform load sharing during the entire range of motion if the location of the optimum instant axis of rotation is not close to that of the motion segment during the entire range of motion. Second, cyclic loading of dynamic stabilization implants may cause fatigue failure of the implant, or the implant-bone junction, e.g. screw loosening. Third, implantation of these systems requires surgery, which may cause new pain from adhesions, or scarring. Moreover, surgery typically involves cutting or stripping ligaments, capsules, muscles, and nerves, which may interfere with the spinal stabilization system.

Functional electrical stimulation (FES) is the application of electrical stimulation to cause muscle contraction to re-animate limbs following damage to the nervous system such as with stroke or spinal cord injury. FES has been the subject of much prior art and scientific publications. In FES, the goal generally is to bypass the damaged nervous system and provide electrical stimulation to nerves or muscles directly which simulates the action of the nervous system. One lofty goal of FES is to enable paralyzed people to walk again, and that requires the coordinated action of several muscles activating several joints. The challenges of FES relate to graduation of force generated by the stimulated muscles, and to the control system for each muscle as well as the system as a whole to produce the desired action such as standing and walking.

With normal physiology, sensors in the muscle, ligaments, tendons and other anatomical structures provide information such as the force a muscle is exerting or the position and velocity of movement of a joint, and that information may be used in the normal physiological control system for limb position and muscle force. This sense is referred to as proprioception. In patients with spinal cord injury, the sensory nervous system is usually damaged as well as the motor system, and thus the afflicted person loses proprioception of what the muscle and limbs are doing. FES systems often seek to reproduce or simulate the damaged proprioceptive system with other sensors attached to a joint or muscle.

For example, in U.S. Pat. No. 6,839,594 to Cohen, a plurality of electrodes are used to activate selected groups of axons in a motor nerve supplying a skeletal muscle in a spinal cord patient (thereby achieving graduated control of muscle force) and one or more sensors such as an accelerometer are used to sense the position of limbs along with electrodes attached to muscles to generate an electromyogram (EMG) signal indicative of muscle activity. In another example, U.S. Pat. No. 6,119,516 to Hock, describes a biofeedback system, optionally including a piezoelectric element, which measures the motions of joints in the body. Similarly, a piezoelectric crystal may be used as a muscle activity sensor as described by U.S. Pat. No. 5,069,680 to Grandjean.

FES has also been used to treat spasticity, characterized by continuous increased muscle tone, involuntary muscle contractions, and altered spinal reflexes which leads to muscle tightness, awkward movements, and is often accompanied by muscle weakness. Spasticity results from many causes including cerebral palsy, spinal cord injury, trauma, and neurodegenerative diseases. U.S. Pat. No. 7,324,853 to Ayal describes apparatus and method for electrically stimulating nerves that supply muscles to modify the muscle contractions that lead to spasticity. The apparatus includes a control system configured to analyze electrical activity of one or more muscles, limb motion and position, and mechanical strain in an anatomical structure.

Ultimately, in many cases the only option left for patients to treat spinal injury is surgical intervention. Spinal fusion, for example, is a standard surgical treatment for chronic back pain. Spine surgery typically involves joining (fusing) bones together to prevent relative motion, and the surgery starts with cutting or stripping ligaments, capsules, muscles, and nerves, to gain access to the spine joints. This may interfere with the spinal stabilization system, and thus there are inherent risks involved with spine surgery procedures.

Iatrogenesis refers to any unforeseen effect on a person resulting from activity conducted by healthcare professionals, e.g., physicians and surgeons, including, but not limited to, injuries following a surgical procedure. Iatrogenesis does not necessarily result from medical errors performed by the surgeon and may include intrinsic adverse effects of a medical procedure.

Currently, it could take between six months to a year or more for a typical patient to recover from spinal fusion surgery. During the recuperation period, patients are advised to avoid twisting, bending, and heavy lifting, to allow the bones to fuse completely and spine stabilization muscles to properly heal. Following a surgical procedure, additional methods may be applied to rehabilitate the spine stabilization muscles to reduce recuperation time. For example, Neuromuscular Electrical Stimulation (NMES) is a subset of the general field of electrical stimulation for muscle contraction, as it is generally applied to nerves and muscles which are anatomically intact, but malfunctioning is a different way. NMES may be delivered via an external system or, in some applications, via an implanted system.

NMES via externally applied skin electrodes has been used to rehabilitate skeletal muscles after injury or surgery in the associated joint. This approach is commonly used to aid in the rehabilitation of the quadriceps muscle of the leg after knee surgery. Electrical stimulation is known to not only improve the strength and endurance of the muscle, but also to restore malfunctioning motor control to a muscle. See, e.g., Gondin et al., "Electromyostimulation Training Effects on Neural Drive and Muscle Architecture", Medicine & Science in Sports & Exercise 37, No. 8, pp. 1291-99 (August 2005).

An implanted NMES system has been used to treat incontinence by stimulating nerves that supply the urinary or anal sphincter muscles. For example, U.S. Pat. No. 5,199,430 to Fang describes implantable electronic apparatus for assisting the urinary sphincter to relax.

The goals and challenges of rehabilitation of anatomically intact (i.e., non-pathological) neuromuscular systems are fundamentally different from the goals and challenges of FES for treating spinal injury patients or people suffering from spasticity. In muscle rehabilitation, the primary goal is to restore normal functioning of the anatomically intact neuromuscular system, whereas in spinal injury and spasticity, the primary goal is to simulate normal activity of a pathologically damaged neuromuscular system.

Still, these methods require intervention by healthcare professionals post-surgery when the patient's muscles have already been weakened due to iatrogenic injury during the spinal surgery.

It would therefore be desirable to provide systems and methods to further reduce recovery time of a patient post-surgery by enhancing function of spine stabilization muscles, e.g., local segmental muscles associated with the lumbar spine stabilization system, prior to or after the planned spine surgery intervention.

SUMMARY OF THE INVENTION

The present invention overcomes the drawbacks of previously-known systems by providing systems and methods for enhancing function to spine stabilization muscles in connection with a planned spine surgery intervention. The pathology that leads to the need for spine surgery often has the effect of interfering with the neuromuscular control system of the spine stabilizing muscles. Therefore, any activity that helps restore normal function to the spine stabilizing system is likely to improve recovery from surgery. In accordance with one aspect of the present invention, spine stabilization muscle function may be enhanced prior to the planned spine surgery intervention. It was applicant's realization that this "prehab" treatment will enhance neural control and function of the patient's spine stabilization muscles during a time period associated with the planned spine surgery intervention, thereby reducing the patient's recovery time following the planned spine surgery intervention. As a result of the prehab treatment, the patient's spine stabilizing muscles will be better functioning prior to the spine surgery intervention, and thus will be less vulnerable to degraded spine stabilization as a result of the spine surgery intervention. In addition, the prehab treatment may strengthen the patient's spine stabilizing muscles such that the muscles are better able to withstand iatrogenic injury caused during the spine surgery intervention, and thus reduce the patient's recovery time post-surgery. For some patients, the prehab treatment may result in improvement that obviates the need for the spine surgery intervention altogether, or as a result of the prehab treatment, surgical intervention may be postponed for some time, e.g., years, thereby satisfying the medical/surgical imperative for conservative treatment.

Specifically, the method for enhancing function of spine stabilizing muscles in connection with a planned spine surgery intervention in a patient's back includes selecting one or more electrodes and a pulse generator in electrical communication with the one or more electrodes. Then, the one or more electrodes are implanted in or adjacent to tissue associated with one or more spine stabilizing muscles within a back of a patient, e.g., a multifidus, transverse abdominis, quadratus lumborum, psoas major, internus abdominis, obliquus externus abdominis, or erector spinae muscles. The method further includes programming the pulse generator for enhancing function of the one or more spine stabilization muscles, and delivering, according to the programming during a time period, e.g., at least 30 days and/or less than 60 days, electrical stimulation from the pulse generator to the tissue associated with the one or more spine stabilization muscles via the one or more electrodes, thereby improving neuromuscular control system performance of the one or more spine stabilizing muscles in connection with the planned spine surgery intervention to reduce the patient's recovery time associated with the planned spine surgery intervention. For example, the time period may be predetermined. In addition, delivering electrical stimulation from the pulse generator to the tissue associated with the one or more spine stabilization muscles may cause contraction of the one or more spine stabilization muscles. Contraction of the one or more spine stabilizing muscles during the time period associated with the planned spine surgery intervention may strengthen the one or more spine stabilizing muscles prior to the planned spine surgery intervention, and/or enhance function of the neuromuscular control system prior to the planned spine surgery intervention.

In accordance with one aspect of the present invention, the one or more electrodes may be implanted in or adjacent to a dorsal ramus nerve that innervates the multifidus muscle such that electrical stimulation is delivered from the pulse generator to the dorsal ramus nerve that innervates the multifidus muscle. In accordance with another aspect of the present invention, the one or more electrodes may be implanted in or adjacent to tissue associated with one or more spine stabilizing muscles prior to the planned spine surgery intervention, and thus, electrical stimulation may be delivered from the pulse generator to the tissue associated with the one or more spine stabilizing muscles during a time period prior to the planned spine surgery intervention, e.g., until a desired goal is achieved.

Further, the one or more electrodes may be disposed on an electrode lead. The electrode lead may have a first anchor angled distally relative to the electrode lead and a second anchor distal to the first anchor angled proximally relative to the electrode lead. Thus, implanting the one or more electrodes in or adjacent to tissue associated with one or more spine stabilizing muscles includes anchoring the electrode lead in or adjacent to tissue associated with one or more skeletal muscles via the first and second anchors.

In addition, programming the pulse generator may include transmitting programming data, e.g., pulse amplitude, pulse width, stimulation rate, stimulation frequency, ramp timing, cycle timing, session timing, or electrode configuration, from an external programmer to the pulse generator, such that electrical stimulation is delivered from the pulse generator to the tissue associated with the one or more spine stabilizing muscles consistent with the programming data. In addition, electrical stimulation may be delivered from the pulse generator to the tissue associated with the one or more spine stabilizing muscles at, e.g., a stimulation rate between 1-30 Hz, a pulse width between 20-500 µs, and a pulse amplitude between 0.1-7 mA, and could be configured to be bipolar, unipolar, or multipolar stimulation. In accordance with another aspect of the present invention, the pulse generator is constructed to be percutaneously implanted such that both the pulse generator and the one or more electrodes may be implanted within the patient's body. Thus, the pulse generator may be implanted within the patient's body prior to delivering electrical stimulation from the pulse generator to the tissue associated with the one or more spine stabilizing muscles via the one or more electrodes. Alternatively, the one or more electrodes may be implanted within the patient's body with one or more lead wires exposed outside the patient's body for coupling with an external pulse generator. Accordingly, at a later time, the one or more electrodes may be decoupled from the external pulse generator, and coupled to a subsequently percutaneously implanted pulse generator.

The method further may include transmitting a stimulation command, e.g., a command to start a treatment session or stop the treatment session; a command to provide telemetry indicating a status of the pulse generator; or a request to conduct an impedance assessment, from an activator to the pulse generator, such that electrical stimulation is delivered from the pulse generator to the tissue associated with the one or more spine stabilizing muscles responsive to the stimulation command. In addition, the method may include sensing muscle contraction via one or more sensors coupled to the pulse generator, and adjusting the electrical stimulation delivered by the pulse generator to maintain smooth and continuous muscle contraction. For example, adjusting the electrical stimulation includes adjusting at least one of pulse amplitude or pulse width of the electrical stimulation. The method also may include removing the one or more electrodes from the patient's body prior to conducting the planned spine surgery intervention.

In accordance with yet another aspect of the present invention, the method further includes reprogramming the pulse generator for restoring muscle function of the one or more skeletal muscles, and delivering, according to the reprogramming and after the planned spine surgery intervention, electrical stimulation from the pulse generator to the tissue associated with the one or more spine stabilizing muscles via the one or more electrodes, thereby facilitating rehabilitation of the one or more spine stabilizing muscles after the planned spine surgery intervention. As will be understood by a person ordinarily skilled in the art, the one or more electrodes may be implanted in or adjacent to tissue associated with one or more spine stabilizing muscles within a back of a patient, e.g., a multifidus, transverse abdominis, quadratus lumborum, psoas major, internus abdominis, obliquus externus abdominis, or erector spinae muscles, at the same time as the spinal surgery. Alternatively, the one or more electrodes may be implanted at a time following the spinal surgery, e.g., some weeks after the spine surgery intervention if, for example, recovery wasn't going as expected. Accordingly, the systems and methods described herein may be used for prehab or rehab treatment.

BRIEF DESCRIPTION OF THE DRAWINGS

FIG. 2A shows an exemplary electrode lead of the stimulator system of FIG. 1.

FIGS. 2B and 2C show alternative orientations of the fixation elements of FIG. 2A, wherein FIG. 2B shows a side view of an exemplary electrode lead and FIG. 2C shows a front view of the lead of FIG. 2B.

DETAILED DESCRIPTION OF THE INVENTION

The neuromuscular stimulation system of the present invention comprises implantable devices for providing electrical stimulation to tissue within a patient's back and external devices for wirelessly communicating programming data and stimulation commands to the implantable devices. The devices disclosed herein may be utilized to stimulate tissue associated with local segmental control of the lumbar spine in accordance with the programming data to enhance function of and strengthen spine stabilizing muscles over a time period in connection with a planned spine surgery intervention, for example, a predetermined period prior to the planned spine surgery intervention. In addition, the devices may be utilized after the planned spine surgery intervention to restore function of and facilitate rehabilitation of the spine stabilizing muscles. In accordance with the principles of the present invention, the stimulator system and methods described herein may be optimized for use in treating back pain of the lumbar spine.

Figure 1:
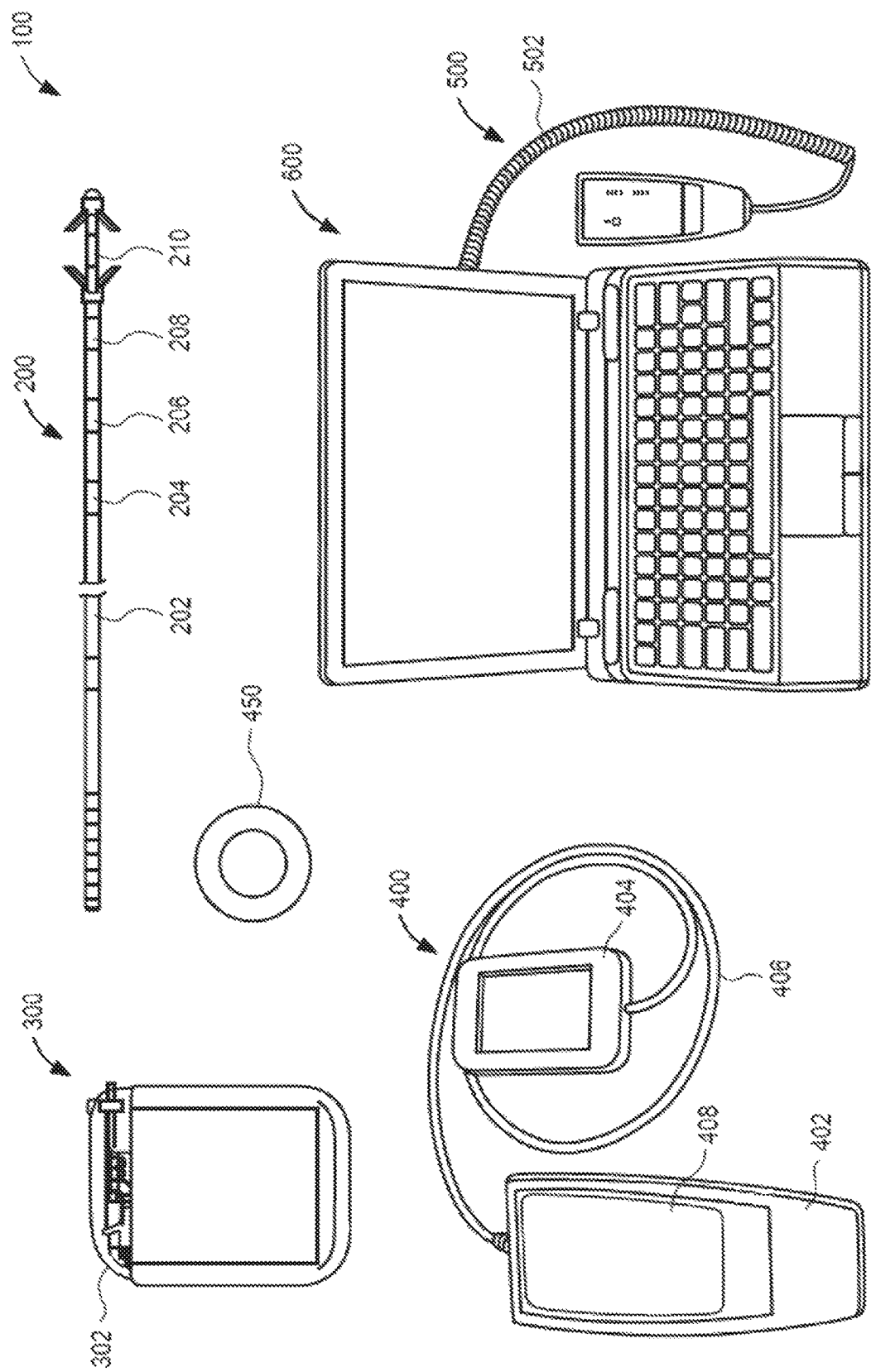
FIG. 1 is a schematic view of an exemplary embodiment of a stimulator system constructed in accordance with the principles of the present invention.

Referring to FIG. 1, an overview of an exemplary stimulator system constructed in accordance with the principles of the present invention is provided. In FIG. 1, components of the system are not depicted to scale on either a relative or absolute basis. Stimulator system 100 includes electrode lead 200, implantable pulse generator (IPG) 300, activator 400, optional magnet 450, external programmer 500, and software-based programming system 600.

Electrode lead 200 includes lead body 202 having a plurality of electrodes, illustratively, electrodes 204, 206, 208, and 210. Electrode lead 200 is configured for implantation in or adjacent to tissue, e.g., nervous tissue, muscle, a ligament, and/or a joint capsule including tissue associated with local segmental control of the lumbar spine. Electrode lead 200 is coupled to IPG 300, for example, via connector block 302. IPG 300 is configured to generate pulses such that electrodes 204, 206, 208, and/or 210 deliver neuromuscular electrical stimulation ("NMES") to target tissue. In one embodiment, the electrodes are positioned to stimulate a peripheral nerve at or near the location where the nerve enters skeletal muscle, which may be one or more of the multifidus, transverse abdominis, quadratus lumborum, psoas major, internus abdominis, obliquus externus abdominis, and erector spinae muscles. Such stimulation may induce contraction of the muscle to restore neural control and rehabilitate the muscle, thereby improving muscle function of local segmental muscles of the lumbar spine, improving lumbar spine stability, and reducing back pain.

IPG 300 is controlled by, and optionally powered by, activator 400, which includes control module 402 coupled to pad 404, e.g., via cable 406. Control module 402 has user interface 408 that permits a user, e.g., patient, physician, caregiver, to adjust a limited number of operational parameters of IPG 300 including starting and stopping a treatment session. Control module 402 communicates with IPG 300 via pad 404, which may comprise an inductive coil or RF transceiver configured to communicate information in a bidirectional manner across a patient's skin to IPG 300 and, optionally, to transmit power to IPG 300.

Stimulator system 100 also may include optional magnet 450 configured to transmit a magnetic field across a patient's skin to IPG 300 such that a magnetic sensor of IPG 300 senses the magnetic field and IPG 300 executes a function that starts or stops a treatment session responsive to the sensed magnetic field.

In FIG. 1, software-based programming system 600 is installed and runs on a conventional laptop computer, "smart phone", tablet, or similar device with computing power, and is used by the patient's physician together with external programmer 500 to provide programming to IPG 300. During patient visits, external programmer 500 may be coupled, either wirelessly or using a cable such as cable 502, to the physician's computer such that software-based programming system 600 may download for review data stored on IPG 300 via external programmer 500. Software-based programming system 600 also may transfer programming data to IPG 300 via external programmer 500 to reprogram stimulation parameters programmed into IPG 300. For example, programming system 600 may be used to program and adjust parameters such as pulse amplitude (voltage or current), pulse width, stimulation rate, stimulation frequency, ramp timing, cycle timing, session timing, and electrode configuration. Programming system 600 also may be configured to upload and store data retrieved from IPG 300 to a remote server for later access by the physician.

Referring now to FIGS. 2A-2C, various embodiments of an exemplary electrode lead are described. In FIG. 2A, an exemplary embodiment of electrode lead 200 is described. Electrode lead 200 contains a plurality of electrodes 204, 206, 208, and 210, disposed at distal end 211 of lead body 202, that are configured to be implanted in or adjacent to tissue, such as nervous tissue, muscle, ligament, and/or joint capsule. Lead body 202 is a suitable length for positioning the electrodes in or adjacent to target tissue while IPG is implanted in a suitable location, e.g., the lower back. For example, lead body 202 may be between about 30 and 80 cm in length, and preferably about 45 or about 65 cm in length. Lead body 202 is also of a suitable diameter for placement, for example, between about 1 and 2 mm in diameter and preferably about 1.3 mm. Electrodes 204, 206, 208, and 210 may be configured to stimulate the tissue at a stimulation frequency and at a level and duration sufficient to cause muscle to contract and may be ring electrodes, partial electrodes, segmented electrodes, nerve cuff electrodes placed around the nerve innervating the target muscle, or the like. Electrodes 204, 206, 208, 210 are a suitable length(s) and spaced apart a suitable distance along lead body 202. For example, electrodes 204, 206, 208, 210 may be about 2-5 mm in length, and preferably about 3 mm, and may be spaced apart about 2-6 mm, and preferably about 4 mm. As will also be understood by one of skill in the art, an electrode lead may contain more or fewer than four electrodes.

Also at distal end 210, first and second fixation elements 212 and 214 are coupled to lead body 202 via first and second fixation rings 216 and 218, respectively. First and second fixation elements 212 and 214 are configured to sandwich an anchor site, e.g., muscle, therebetween to secure electrode lead 200 at a target site without damaging the anchor site. First and second fixation elements 212 and 214 may include any number of projections, generally between 1 and 8 each and preferably 3 or 4 each. The radial spacing between the projections along the respective fixation ring is defined by the anchor site around which they are to be placed. Preferably, the projections of first and second fixation elements 212 and 214 are equidistantly spaced apart radially, i.e., 180 degrees with two projections, 120 degrees with three projections, 90 degrees with four projections, etc.

First fixation elements 212 are angled distally relative to lead body 202, and resist motion in the first direction and prevent, in the case illustrated, insertion of the lead too far, as well as migration distally. Second fixation elements 214 are angled proximally relative to lead body 202 and penetrate through a tissue plane and deploy on the distal side of the tissue immediately adjacent to the target of stimulation. First fixation elements 212 are configured to resist motion in the opposite direction relative to second fixation elements 214. This combination prevents migration both proximally and distally, and also in rotation. In the illustrated embodiment, first fixation elements 212 are positioned between electrode 208 and distal most electrode 210 and second fixation element 214 is positioned between distal most electrode 210 and end cap 220. The length of and spacing between the fixation elements is defined by the structure around which they are to be placed. In one embodiment, the length of each fixation element is between about 1.5-4 mm and preferably about 2.5 mm and the spacing is between about 2 mm and 10 mm and preferably about 6 mm. First and second fixation elements 212 and 214 are configured to fold inward toward lead body 202 in a delivery state and to expand, e.g., due to retraction of a sheath, in a deployed state. While FIG. 2A illustrates fixation elements 212 and 214 on lead body 202, it should be understood that other fixation elements may be used to anchor electrode lead 200 at a suitable location including the fixation elements described in U.S. Pat. No. 9,079,019 to Crosby and U.S. Pat. No. 9,999,763 to Shiroff, both assigned to the assignee of the present invention, the entire contents of each of which are incorporated herein by reference.

Referring now to FIGS. 2B and 2C, an alternative embodiment of electrode lead 200 is described. Electrode lead 200' is constructed similarly to electrode lead 200 of FIG. 2A, wherein like components are identified by like-primed reference numbers. Thus, for example, lead body 202' in FIGS. 2B and 2C corresponds to lead body 202 of FIG. 2A, etc. As will be observed by comparing FIGS. 2B and 2C with FIG. 2A, electrode lead 200' includes fixation elements that are radially offset with respect to each other. For example, first fixation elements 212' may be configured to be radially offset relative to second fixation elements 214' by prefabricating at least one of first fixation ring 216' and second fixation ring 218' relative to lead body 202' such that at least one of first fixation elements 212' and second fixation elements 214' is radially offset with respect to the other. For example, as illustrated in FIG. 2C, first fixation elements 212' has three projections 203 and second fixation elements 214' has three projections 205 and, preferably, projections 203 are radially offset relative to projections 205 by a predetermined angle, e.g., approximately 60 degrees. However, as appreciated by one of ordinary skill in the art, projections 203 may be radially offset relative to projections 205 by other angles to achieve the benefits in accordance with the present invention described below. Projections 203 and 205 may be formed of a flexible material, e.g., a polymer, and may be collapsible and self-expandable when deployed. For example, projections 203 and 205 may collapse inward toward lead body 202' in a delivery state such that projections 203 and 205 are generally parallel to the longitudinal axis of lead body 202' within a sheath. In the delivery state, the radially offset first and second fixation elements 212' and 214' need not overlap within a sheath. Further, projections 203 and 205 may expand, e.g., due to retraction of the sheath, in a deployed state such that projections 203 are angled distally relative to lead body 202', and resist motion in the first direction and prevent, in the case illustrated, insertion of the lead too far, as well as migration distally, and projections 205 are angled proximally relative to lead body 202' to resist motion in an opposite direction relative to first fixation elements 212'. This combination prevents migration of the lead both proximally and distally, and also in rotation.

Lead body 202 further includes stylet lumen 222 extending therethrough. Stylet lumen 222 is shaped and sized to permit a stylet to be inserted therein, for example, during delivery of electrode lead 200. In one embodiment, end cap 220 is used to prevent the stylet from extending distally out of stylet lumen 222 beyond end cap 220.

Lead body 202 may include an elastic portion as described in U.S. Pat. No. 9,999,763 to Shiroff, or U.S. Patent Application Pub. No. 2014/0350653 to Shiroff, both assigned to the assignee of the present invention, the entire contents of each of which are incorporated herein by reference.

At proximal end 224, electrode lead 200 includes contacts 226, 228, 230, and 232 separated along lead body 202 by spacers 234, 236, 238, 240, and 242. Contacts 226, 228, 230, and 232 may comprise an isodiametric terminal and are electrically coupled to electrodes 204, 206, 208, and 210, respectively, via, for example, individually coated spiral wound wires. A portion of proximal end 224 is configured to be inserted in IPG 300 and set-screw retainer 244 is configured to receive a screw from IPG 300 to secure the portion of electrode lead 200 within IPG 300.

As would be apparent to one of ordinary skill in the art, various electrode locations and configurations would be acceptable, including the possibility of skin surface electrodes. The electrode(s) may be an array of a plurality of electrodes, or may be a simple single electrode where the electrical circuit is completed with an electrode placed elsewhere (not shown) such as a skin surface patch or by the metal housing of an implanted pulse generator. In addition, electrode lead 200 may comprise a wirelessly activated or leadless electrode, such as described in U.S. Pat. No. 8,321,021 to Kisker, such that no lead need be coupled to IPG 300.

Figure 3A:
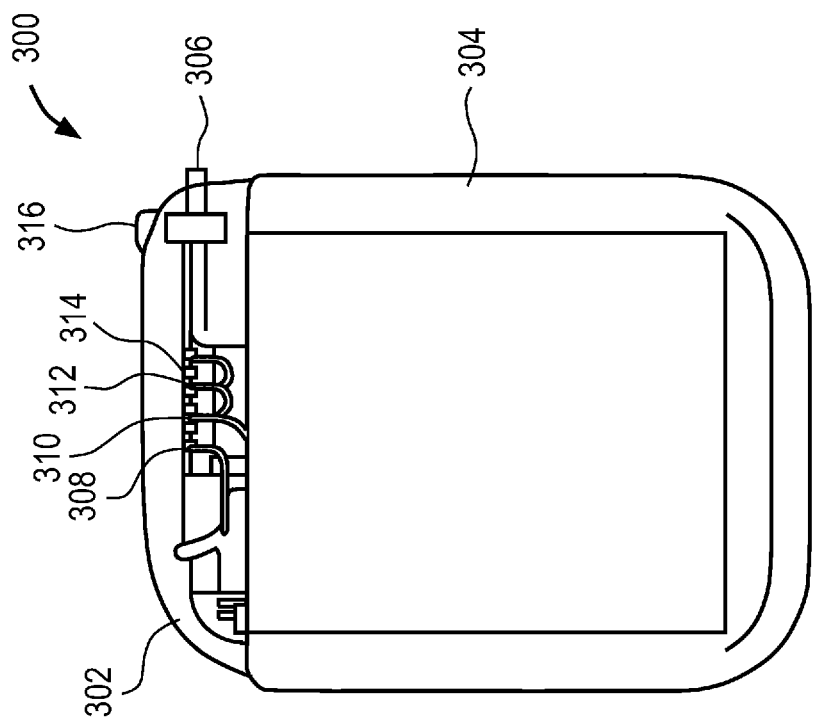
FIG. 3A shows an exemplary implantable pulse generator (IPG) of the stimulator system of FIG. 1.

Referring to FIG. 3A, IPG 300 is configured to generate pulses for electrical transmission to electrode lead 200. As is common with other active implantable medical devices, the IPG electronics are housed in a hermetically sealed metal housing 304. Housing 304 may comprise titanium or other biocompatible material, and includes connector block 302 that permits electrode lead 200 to be electrically coupled to the electronics within housing 304 via channel 306. Channel 306 is coupled to conductors 308, 310, 312, and 314 which are coupled to the IPG electronics. When proximal end 224 of electrode lead 200 is inserted within channel 306, conductors 308, 310, 312, and 314 are electrically coupled to contacts 226, 228, 230, and 232, respectively, and, in turn, electrically coupled to electrodes 204, 206, 208, and 210, respectively. Set-screw 316 is configured to be tightened down on set-screw retainer 244 to secure a portion of electrode lead 200 within channel 306. IPG 300 further includes a second channel (not shown) with four additional conductors. The two separate channels facilitate bilateral stimulation and the electrode configuration, e.g., combination of positive and negative electrodes, may be programmed independently for each channel.

As will be appreciated by one of ordinary skill in the art, while IPG 300 is illustratively implantable, a stimulator may be disposed external to a body of a patient on a temporary or permanent basis without departing from the scope of the present invention. For example, an external stimulator may be coupled to the electrodes wirelessly.

Figure 3B:
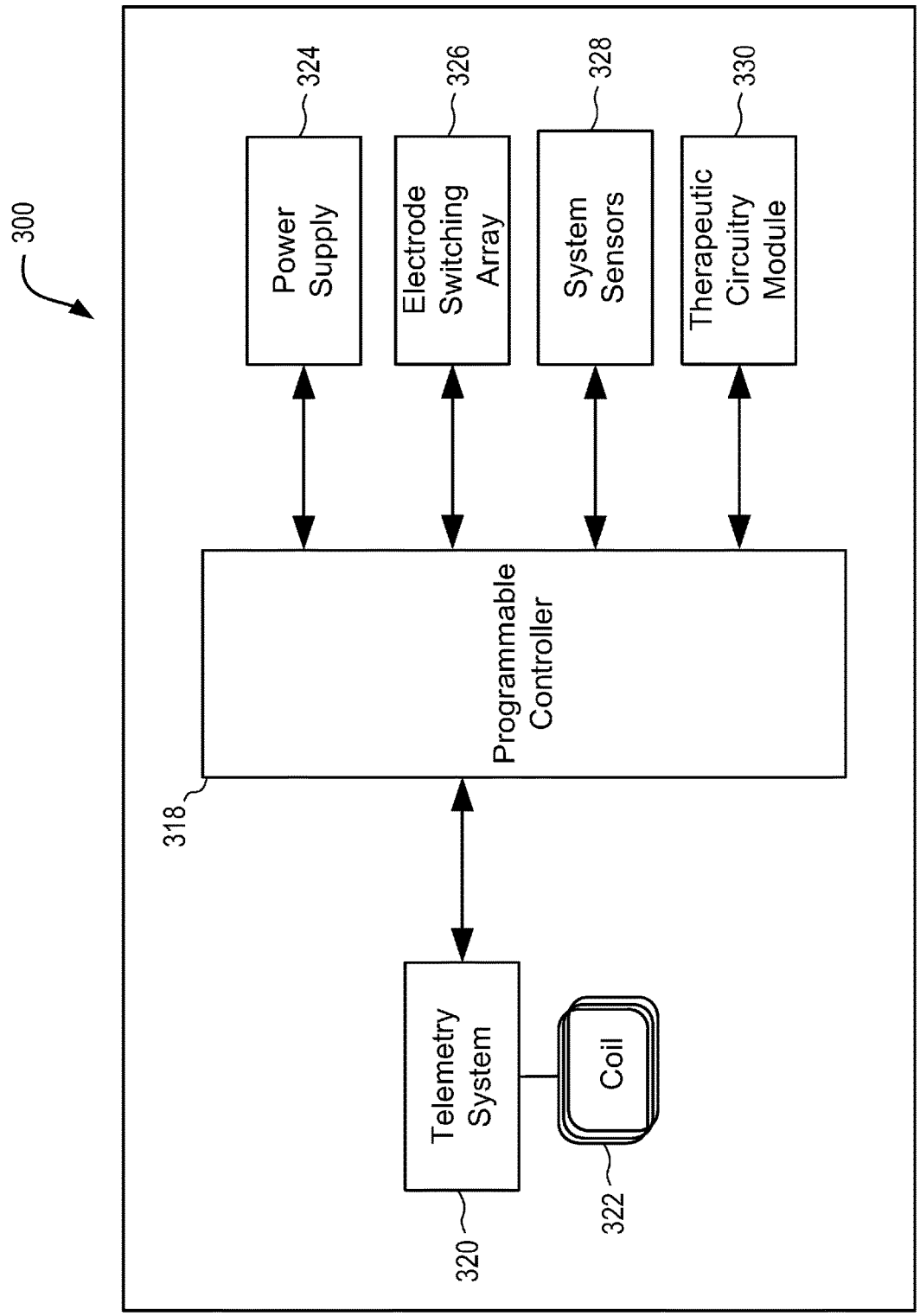
FIGS. 3B through 3D show alternative generalized block diagrams of the IPG of FIG. 3A, wherein the IPG of FIG. 3B has an inductive communications circuit, the IPG of FIG. 3C has a RF transceiver communications circuit, and the IPG of FIG. 3D has an inductive communications circuit and a RF transceiver communications circuit.

With respect to FIG. 3B, a generalized schematic diagram of the internal functional components of IPG 300 is now described. IPG 300 may include programmable controller 318, telemetry system 320 coupled to coil 322, power supply 324, electrode switching array 326, system sensors 328, and optional therapeutic circuitry module 330.

Controller 318 is electrically coupled to, and configured to control, the internal functional components of IPG 300. Controller 318 may comprise a commercially available microcontroller unit including a programmable microprocessor, volatile memory, nonvolatile memory such as EEPROM for storing programming, and nonvolatile storage, e.g., Flash memory, for storing firmware and a log of system operational parameters and patient data. The memory of controller 318 stores program instructions that, when executed by the processor of controller 318, cause the processor and the functional components of IPG 300 to provide the functionality ascribed to them herein. Controller 318 is configured to be programmable such that programming data is stored in the memory of controller 318 and may be adjusted using external programmer 500 as described below. Programming data may include pulse amplitude (voltage or current), pulse width, stimulation rate, stimulation frequency, ramp timing, cycle timing, session timing, and electrode configuration. In accordance with one embodiment, programmable parameters, their ranges, and nominal values are:

| Parameter | Min | Max | Nominal |
| --- | --- | --- | --- |
| Amplitude | 0 mA | 7.0 mA | 1 mA |
| Pulse Width | 25 μs | 500 μs | 200 μs |
| Rate | 1 Hz | 40 Hz | 20 Hz |
| On Ramp | 0 s | 5 s | 2 s |
| Off Ramp | | | |
| Cycle-On | 2 s | 20 s | 10 s |
| Cycle-Off | 20 s | 120 s | 20 s |
| Session | 1 min | 60 min | 30 min |

Controller 318 may be programmable to allow electrical stimulation between any chosen combination of electrodes on the lead, thus providing a simple bipolar configuration. In addition, controller 318 may be programmed to deliver stimulation pulses in a guarded bipolar configuration (more than 1 anode surrounding a central cathode) or IPG housing 304 may be programmed as the anode, enabling unipolar stimulation from any one of the one or more electrodes.

Controller 318 further may be programmed with a software routine to calculate the impedance at electrode lead 200. For example, controller 318 may direct power supply 324 to send an electrical signal to one or more electrodes which emit electrical power. One or more other electrodes receive the emitted electrical power and send a received signal to controller 318 that runs the routine to calculate impedance based on the sent signal and the received signal.

Controller 318 is coupled to communications circuitry including telemetry system 320, which is electrically coupled to coil 322, that permits transmission of stimulation commands, and optionally power, between IPG 300 and activator 400 such that IPG 300 may be powered, programmed, and/or controlled by activator 400. For example, controller 318 may start or stop a treatment session responsive to stimulation commands received from a corresponding telemetry system and coil of activator 400 via coil 322 and telemetry system 320. Telemetry system 320 and coil 322 further permit transmission of programming data, and optionally power, between IPG 300 and external programmer 500 such that IPG 300 may be powered, programmed, and/or controlled by software-based programming system 600 via external programmer 500. For example, controller 318 may direct changes to at least one of pulse amplitude (voltage or current), pulse width, stimulation rate, stimulation frequency, ramp timing, cycle timing, session timing, and electrode configuration responsive to programming data received from a corresponding telemetry system and coil of external programmer 500 via coil 322 and telemetry system 320.

The technology for telemetry system 320 and coil 322 is well known to one skilled in the art and may include a magnet, a short range telemetry system, a longer range telemetry system (such as using MICS RF Telemetry available from Zarlink Semiconductor of Ottawa, Canada), or technology similar to a pacemaker programmer. Alternatively, coil 322 may be used to transmit power only, and separate radio frequency transmitters may be provided in IPG 300 activator 400, and/or external programmer 500 for establishing bidirectional or unidirectional data communication.

Power supply 324 powers the electrical components of IPG 300, and may comprise a primary cell or battery, a secondary (rechargeable) cell or battery or a combination of both. Alternatively, power supply 324 may not include a cell or battery, but instead comprise a capacitor that stores energy transmitted through the skin via a Transcutaneous Energy Transmission System (TETs), e.g., by inductive coupling. In a preferred embodiment, power supply 324 comprises a lithium ion battery.

Controller 318 further may be coupled to electrode switching array 326 so that any subset of electrodes of the electrode leads may be selectively coupled to therapeutic circuitry module 330, described in detail below. In this way, an appropriate electrode set may be chosen from the entire selection of electrodes implanted in the patient's body to achieve a desired therapeutic effect. Electrode switching array 326 preferably operates at high speed, thereby allowing successive stimulation pulses to be applied to different electrode combinations.

System sensors 328 may comprise one or more sensors that monitor operation of the systems of IPG 300, and log data relating to system operation as well as system faults, which may be stored in a log for later readout using software-based programming system 600. In one embodiment, system sensors 328 include a magnetic sensor configured to sense a magnetic field and to transmit a signal to controller 318 based on the sensed magnetic field such that the controller executes a function such as starting or stopping a treatment session. In another embodiment, system sensors 328 include one or more sensors configured to sense muscle contraction and to generate a sensor signal based on the muscle contraction. Controller 318 is configured to receive the sensor signal from system sensors 328 and to adjust the stimulation parameters based on the sensor signal. In one embodiment, system sensors 328 sense an increase or decrease in muscle movement and controller 318 increases or decreases the stimulation frequency to maintain smooth and continuous muscle contraction.

In one embodiment, sensors 328 may include an accelerometer that senses acceleration of a muscle caused by muscle contraction. The accelerometer may be a 1-, 2- or 3-axis analog or digital accelerometer that determines whether the patient is active or asleep or senses overall activity of the patient, which may be a surrogate measure for clinical parameters (e.g., more activity implies less pain), and/or a heart rate or breathing rate (minute ventilation) monitor, e.g., which may be obtained using one or more of the electrodes disposed on the electrode leads. The accelerometer may be used to determine the orientation of IPG 300, and by inference the orientation of the patient, at any time.

For example, after implantation, software-based programming system 600 may be used to take a reading from the implant, e.g., when the patient is lying prone, to calibrate the orientation of the accelerometer. If the patient is instructed to lie prone during therapy delivery, then the accelerometer may be programmed to record the orientation of the patient during stimulation, thus providing information on patient compliance. In other embodiments, system sensors 328 may include a pressure sensor, a movement sensor, and/or a strain gauge configured to sense muscle contraction and to generate a sensor signal based on the muscle contraction, and in a further embodiment, various combinations of at least one of an accelerometer, a pressure sensor, a movement sensor, and/or a strain gauge are included.

Sensors 328 may also include, for example, a humidity sensor to measure moisture within housing 304, which may provide information relating to the state of the electronic components, or a temperature sensor, e.g., for measuring battery temperature during charging to ensure safe operation of the battery. Data from the system sensors may be logged by controller 318 and stored in nonvolatile memory for later transmission to software-based programming system 600 via external programmer 500.

As will be appreciated by one of ordinary skill in the art, system sensors 328 may be placed in a variety of locations including within housing 302, within or adjacent to the tissue that is stimulated, and/or in proximity to the muscle to be contracted and connected via a separate lead to IPG 300. In other embodiments, sensors 324 may be integrated into one or more of the leads used for stimulation or may be an independent sensor(s) operatively coupled to IPG 300 using, for example, radio frequency (RF) signals for transmitting and receiving data.

Controller 318 also may be coupled to optional therapeutic circuitry module 330 that provides any of a number of complimentary therapeutic stimulation, analgesic, feedback or ablation treatment modalities as described in detail below. IPG 300 illustratively includes one therapeutic circuitry module 330, although additional circuitry modules may be employed in a particular embodiment depending upon its intended application, as described in U.S. Patent Application Publication No. 2011/0224665 to Crosby, assigned to the assignee of the present invention, the entire contents of which are incorporated herein by reference. Therapeutic circuitry module 330 may be configured to provide different types of stimulation, either to induce muscle contractions or to block pain signals in afferent nerve fibers; to monitor muscle contractions induced by stimulation and adjust the applied stimulation regime as needed to obtain a desired result; or to selectively and intermittently ablate nerve fibers to control pain and thereby facilitate muscle rehabilitation.

Figure 3C:
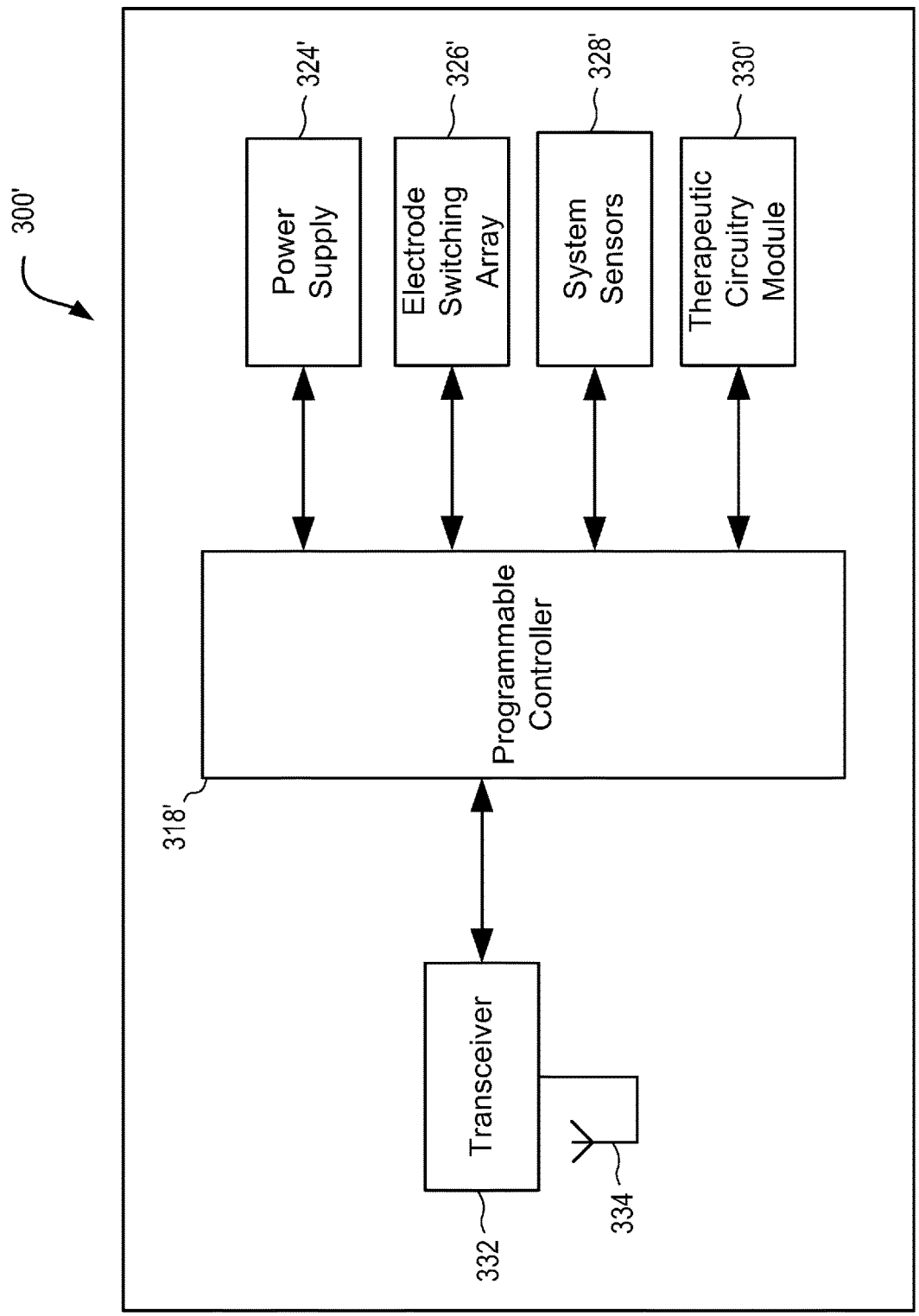

Referring to FIG. 3C, IPG 300' is constructed similarly to IPG 300 of FIG. 3B, wherein like components are identified by like-primed reference numbers. Thus, for example, power supply 324' in FIG. 3C corresponds to power supply 324 of FIG. 3B, etc. As will be observed by comparing FIGS. 3B and 3C, IPG 300' includes a communications circuit employing transceiver 332 coupled to antenna 334 (which may be inside or external to the hermetic housing) rather than telemetry system 320 and coil 322 of IPG 300.

Transceiver 332 preferably comprises a radio frequency (RF) transceiver and is configured for bi-directional communications via antenna 334 with a similar transceiver circuit disposed in activator 400 and/or external programmer 500. For example, transceiver 332 may receive stimulation commands from activator 400 and programming data from software-based programming system 600 via external programmer 500. Controller 318 may direct changes to at least one of pulse amplitude (voltage or current), pulse width, stimulation rate, stimulation frequency, ramp timing, cycle timing, session timing, and electrode configuration, including commands to start or stop a treatment session, responsive to programming data and/or stimulation commands received from a corresponding transceiver and antenna of activator 400 and/or external programmer 500 via antenna 334 and transceiver 332. Transceiver 332 also may include a low power mode of operation, such that it periodically awakens to listen for incoming messages and responds only to those messages including the unique device identifier assigned to that IPG. In addition, transceiver 332 may employ an encryption routine to ensure that messages sent from, or received by, IPG 300 cannot be intercepted or forged.

Figure 3D:
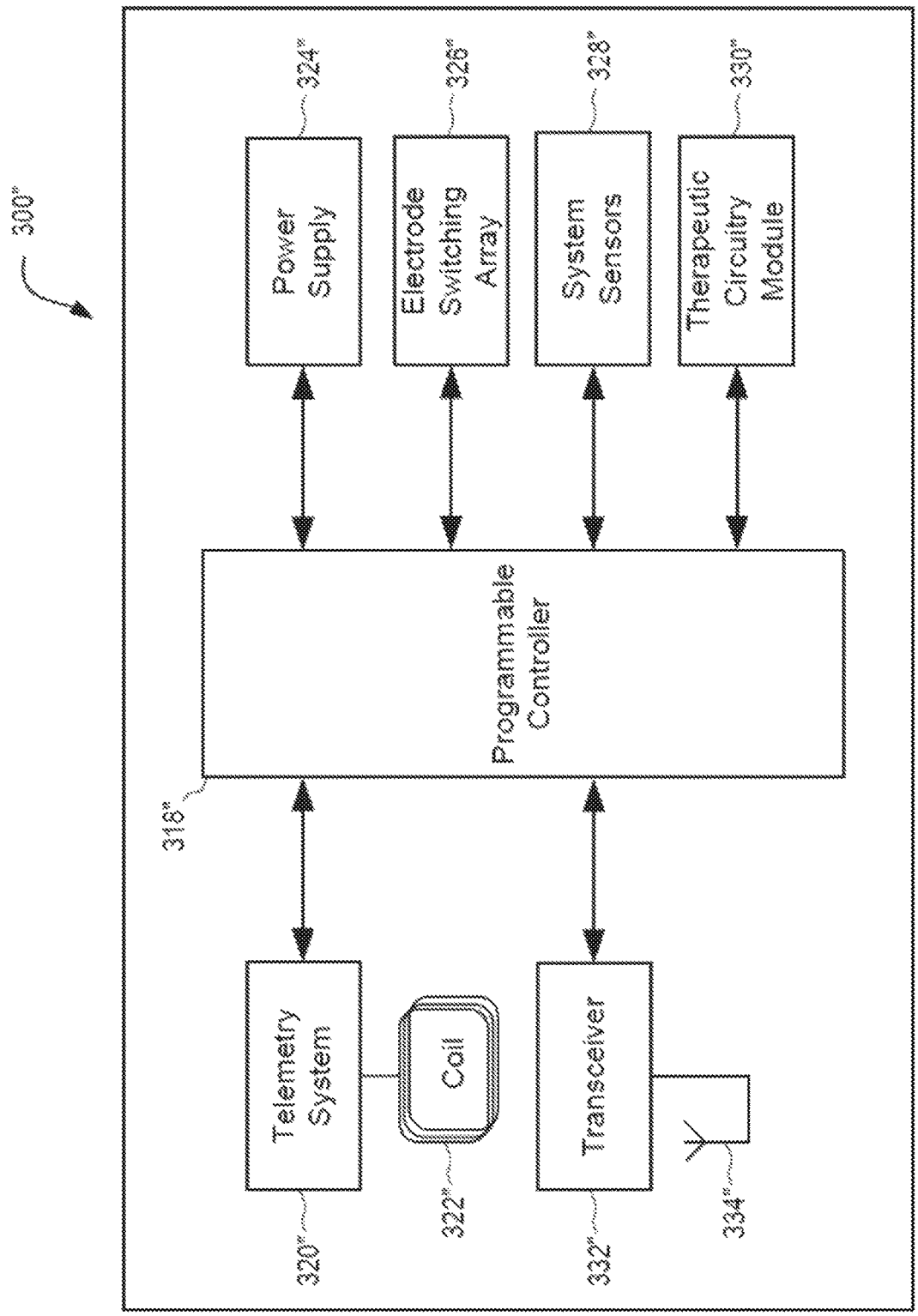

Referring to FIG. 3D, IPG 300" is constructed similarly to IPG 300 of FIG. 3B and IPG 300' of FIG. 3C except that IPG 300" includes a communications circuit employing telemetry system 320" and coil 322" and a communications circuit employing transceiver 332" and antenna 334". IPG 300" is preferably in an embodiment where IPG 300" communicates inductively and using RF. In one embodiment, telemetry system 320" and coil 322" are configured to transfer stimulation commands, and optionally power, between IPG 300" and activator 400 from a corresponding telemetry system and coil of activator 400. In such an embodiment, transceiver 332" and antenna 334" are configured to transfer programming data between IPG 300" and external programmer 500' from a corresponding transceiver and antenna of external programmer 500'. In an alternative embodiment, telemetry system 320" and coil 322" permit transfer of programming data, and optionally power, between IPG 300" and external programmer 500 from a corresponding telemetry system and coil of external programmer 500. In such an embodiment, transceiver 332" and antenna 334" are configured for transfer of stimulation commands between IPG 300" and activator 400' from a corresponding transceiver and antenna of activator 400'.

Figure 4A:
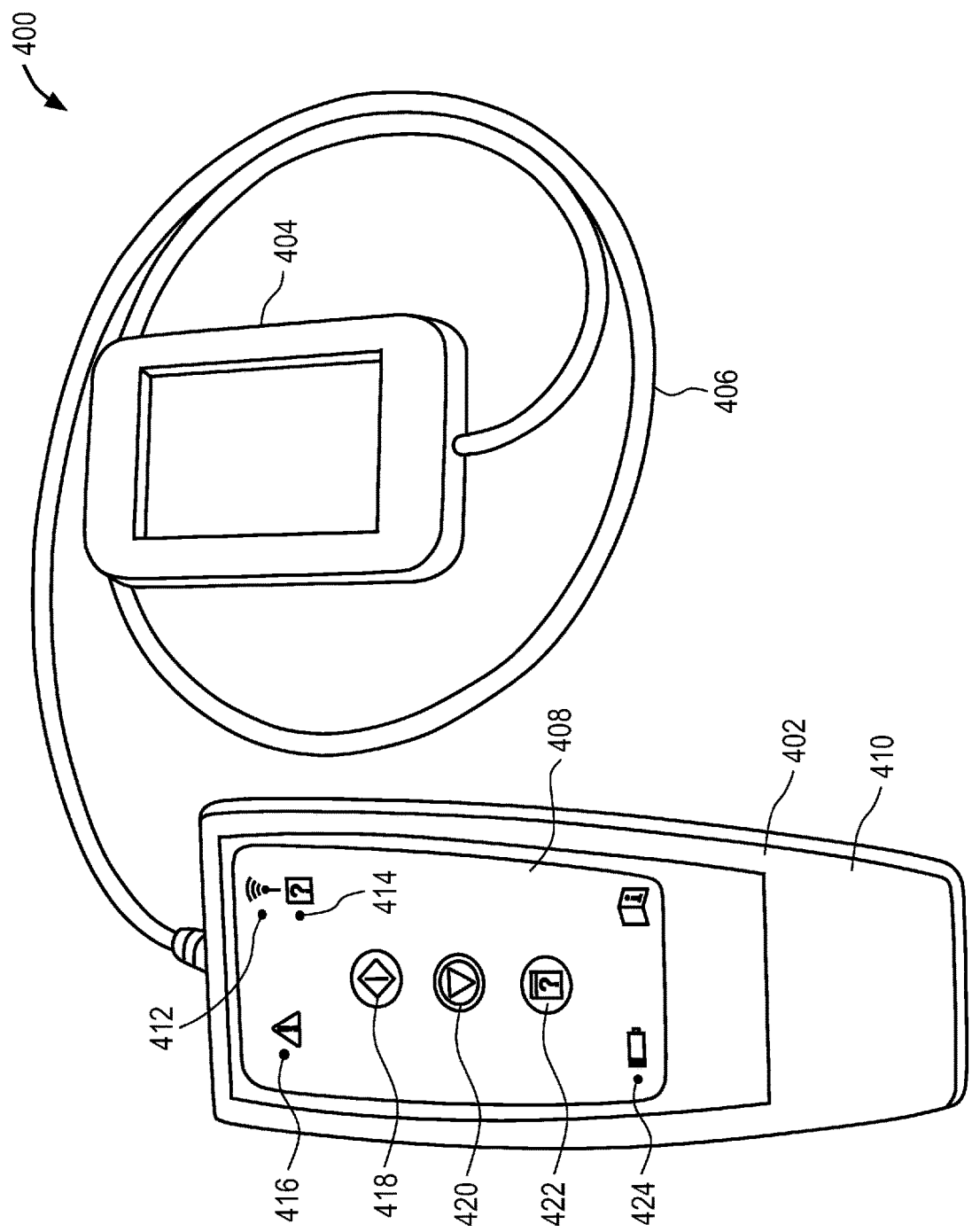
FIG. 4A shows an exemplary activator of the stimulator system of FIG. 1.

Referring now to FIG. 4A, exemplary activator 400, including control module 402 and pad 404, is described. Control module 402 includes housing 410 sized for handheld use and user interface 408. User interface 408 permits a user, e.g., patient, physician, caregiver, to adjust a limited number of operational parameters of IPG 300 including starting and stopping a treatment session. Illustratively, user interface 408 includes signal LED 412, status LED 414, warning LED 416, start button 418, stop button 420, status button 422, and battery LED 424. Signal LED 412 preferably contains multiple diodes, each of which emit light of a different preselected color. Signal LED 412 is configured to illuminate when the communications circuit within pad 404 detects a suitable connection with the corresponding communications circuit in IPG 300 suitable for power transmission and/or data communication between IPG 300 and activator 400. In one embodiment, signal LED 412 illuminates a red diode when there is not a suitable connection, a yellow diode when the connection is suitable but weak, and a green diode when the connection is suitable and strong. Status LED 414 also may include multiple diodes that illuminate in a pattern of flashes and/or colors to indicate to the user the status of IPG 300. Such patterns are stored in the memory of the controller of control module 402 and may indicate whether the IPG is directing stimulation to occur or awaiting commands. A user may refer to a user manual to decode a pattern shown on status LED 414. Warning LED 416 is configured to illuminate when the controller of control module 402 detects an error and indicates that a user should contact their physician or clinic. When start button 418 is pressed, the controller of control module 402 directs a signal to be sent to IPG 300 via pad 404 and cable 406 to begin a treatment session. When stop button 420 is pressed, the controller of control module 402 directs a signal to be sent to IPG 300 via pad 404 and cable 406 to end a treatment session. Alternatively, the treatment session may have a predetermined length and the controller de-energizes the electrodes when the session time expires. Battery LED 424 is configured to illuminate when the controller in control module 402 detects that the battery levels are below a predetermined threshold.

Pad 404 is configured to communicate information and, optionally, transfer power from control module 402 to IPG 300 in a bidirectional manner across a patient's skin. In one embodiment, pad 404 includes an inductive coil within its housing. Cable 406 is a suitable length so that a patient may comfortably place pad 404 in extracorporeal proximity to IPG 300 implanted in the patient's lower back while viewing control module 402 to confirm correct placement using signal LED 412.

Figure 4B:
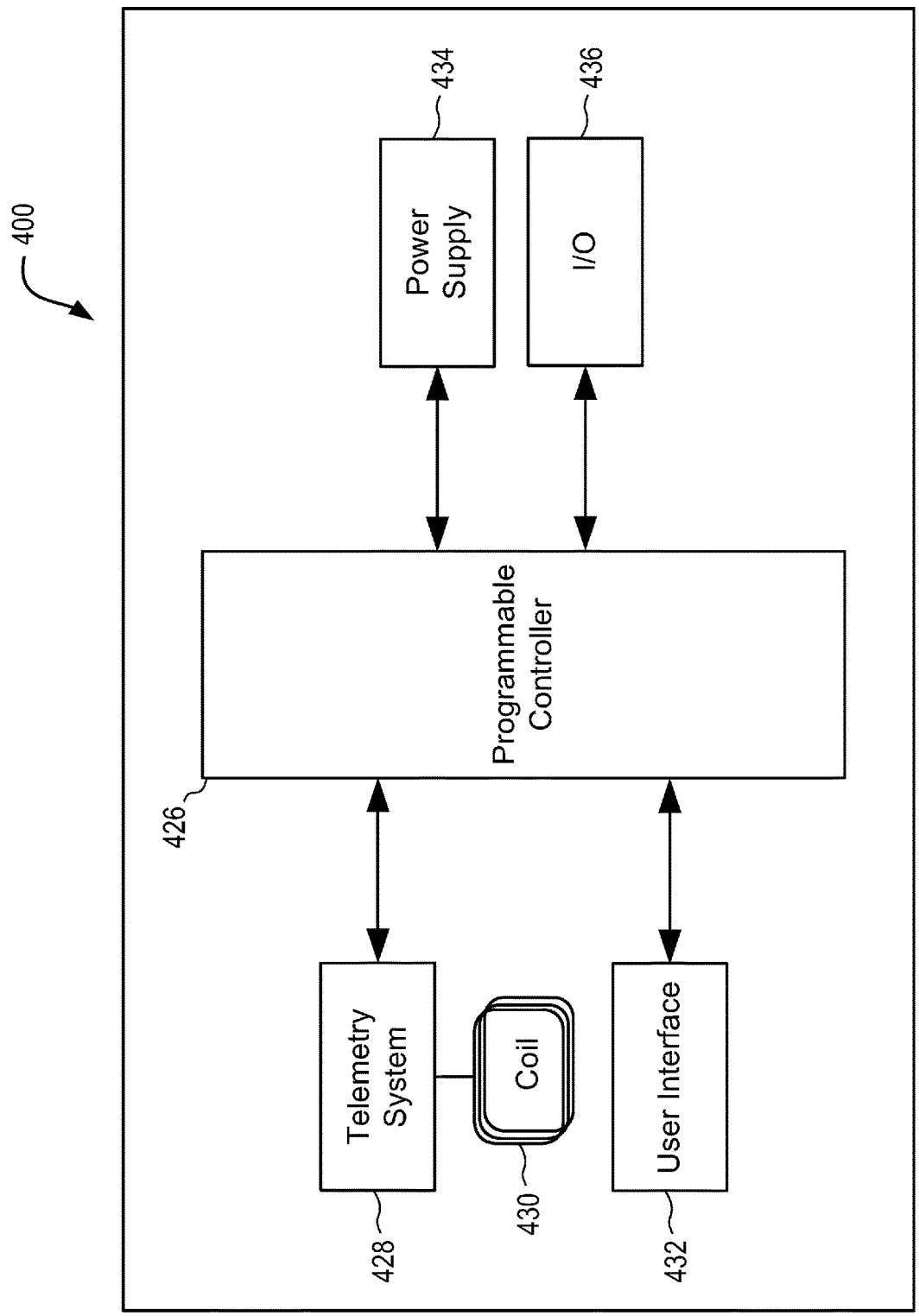
FIGS. 4B and 4C show alternative generalized block diagrams of the activator of FIG. 4A, wherein the activator of FIG. 4B has an inductive communications circuit and the activator of FIG. 4C has a RF transceiver communications circuit.

With respect to FIG. 4B, a generalized schematic diagram of the internal functional components of activator 400 is now described. Activator 400 may include programmable controller 426, telemetry system 428 coupled to coil 430, user interface 432, power supply 434, and input and output circuitry (I/O) 436. In a preferred embodiment, programmable controller 426, telemetry system 428, user interface 432, power supply 434, and input and output circuitry (I/O) 436 are housed within control module housing 410 and coil 430 is housed within the housing for pad 404.

Controller 426 is electrically coupled to, and configured to control, the internal functional components of activator 400. Controller 426 may comprise a commercially available microcontroller unit including a programmable microprocessor, volatile memory, nonvolatile memory such as EEPROM for storing programming, and nonvolatile storage, e.g., Flash memory, for storing firmware and a log of system operational parameters and patient data. The memory of controller 426 may store program instructions that, when executed by the processor of controller 426, cause the processor and the functional components of activator 400 to provide the functionality ascribed to them herein. Controller 426 is configured to be programmable. For example, controller 426 may send stimulation commands responsive to user input received at user interface 432 to controller 318 of IPG 300 via the telemetry (or RF) systems to start or stop a treatment session. In a preferred embodiment, a limited number of stimulation parameters may be adjusted at user interface 432 to minimize the chance of injury or inappropriate stimulation caused by adjustments made by non-physician users. In an alternative embodiment, controller 426 also may send adjustments to stimulation parameters, e.g., pulse amplitude (voltage or current), pulse width, stimulation rate, stimulation frequency, ramp timing, cycle timing, session timing, and electrode configuration to IPG 300 responsive to user input received at user interface 432.

Controller 426 is coupled to telemetry system 428, which is electrically coupled to coil 430 (e.g., via cable 406), that permits transmission of energy and stimulation commands between activator 400 and IPG 300 (or IPG 300") such that IPG 300 may be powered, programmed, and/or controlled by activator 400 responsive to user input received at user interface 432. For example, controller 426 may direct telemetry system 428 and coil 430 to send adjustments to stimulation parameter(s), including commands to start or stop a treatment session or provide status of the IPG, responsive to user input received at user interface 432 to coil 322 and telemetry system 320 of IPG 300. The technology for telemetry system 428 and coil 430 is well known to one skilled in the art and may be similar to telemetry system 320 and coil 322 described above. Alternatively, coil 430 may be used to transmit power only, and separate radio frequency transmitters may be provided in activator 400 and IPG 300 for establishing bidirectional or unidirectional data communication.

User interface 432 is configured to receive user input and to display information to the user. As described above, user interface 432 may include buttons for receiving user input and LEDs for displaying information to the user. As will be readily apparent to one skilled in the art, user interface 432 is not limited thereto and may use a display, a touch screen, a keypad, a microphone, a speaker, a trackball, or the like.

Power supply 434 powers the electrical components of activator 400, and may comprise a primary cell or battery, a secondary (rechargeable) cell or battery or a combination of both. Alternatively, power supply 434 may be a port to allow activator 400 to be plugged into a conventional wall socket for powering components.

Input and output circuitry (I/O) 436 may include ports for data communication such as wired communication with a computer and/or ports for receiving removable memory, e.g., SD card, upon which program instructions or data related to activator 400 use may be stored.

Figure 4C:
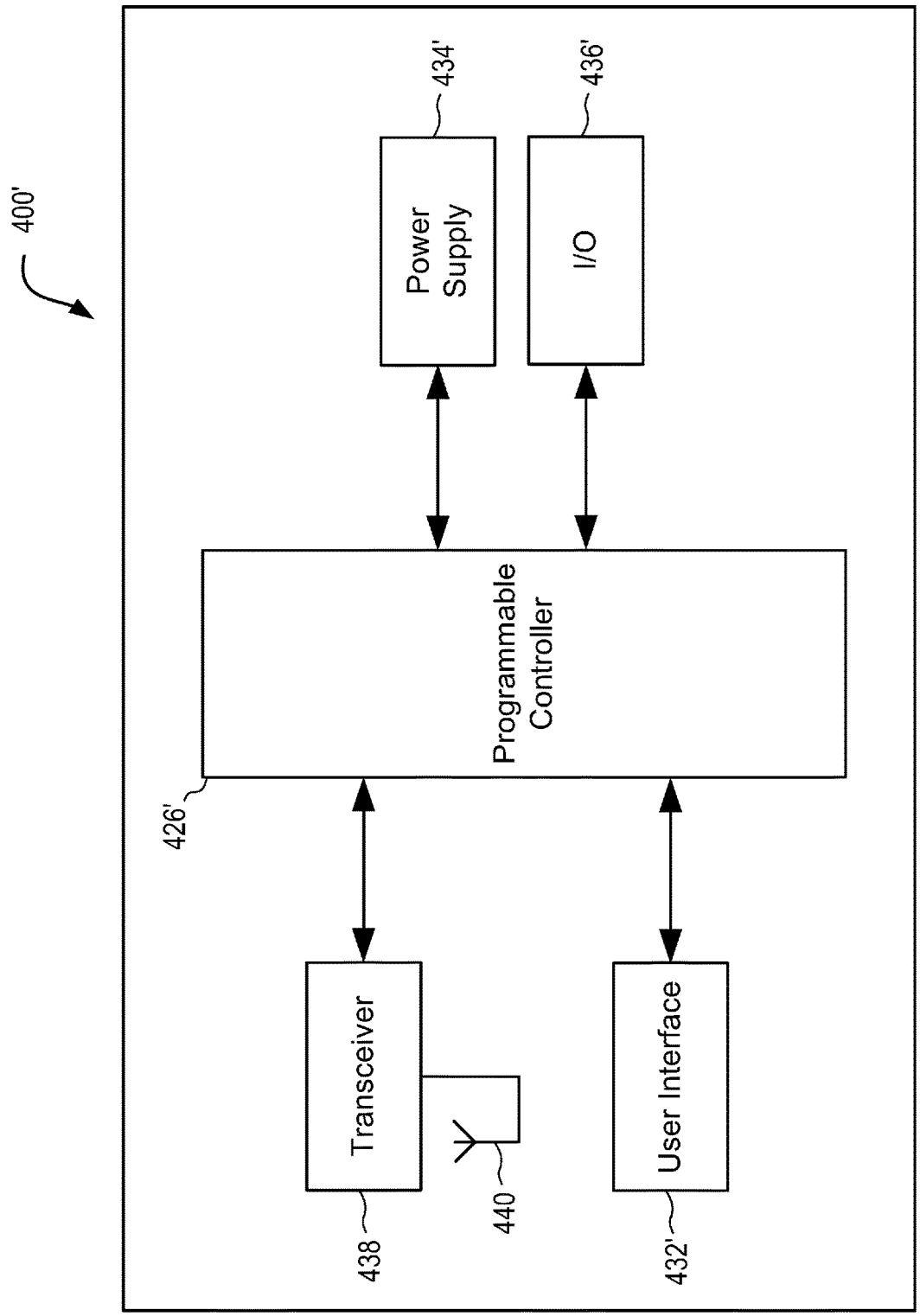

Referring to FIG. 4C, activator 400' is constructed similarly to activator 400 of FIG. 4B except that activator 400' includes a communications circuit employing transceiver 438 and antenna 440 rather than a communications circuit employing telemetry system 428 and coil 430. Transceiver 438 preferably comprises a radio frequency (RF) transceiver and is configured for bi-directional communications via antenna 440 with transceiver 332 via antenna 334 of IPG 300'. Transceiver 438 may transmit stimulation commands from activator 400' to IPG 300' (or IPG 300"). For example, controller 426' may direct transceiver 438 to transmit commands to start or stop a treatment session to IPG 300' responsive to user input received at user interface 432'. In one embodiment, controller 426' may direct transceiver 438 to transmit a command to provide status of IPG 300' or commands to adjust stimulation parameter(s) to IPG 300' responsive to user input received at user interface 432'.

Transceiver 438 also may include a low power mode of operation, such that it periodically awakens to listen for incoming messages and responds only to those messages including the unique device identifier assigned to that activator. In addition, transceiver 438 may employ an encryption routine to ensure that messages sent from, or received by, activator 400' cannot be intercepted or forged.

Figure 5A:
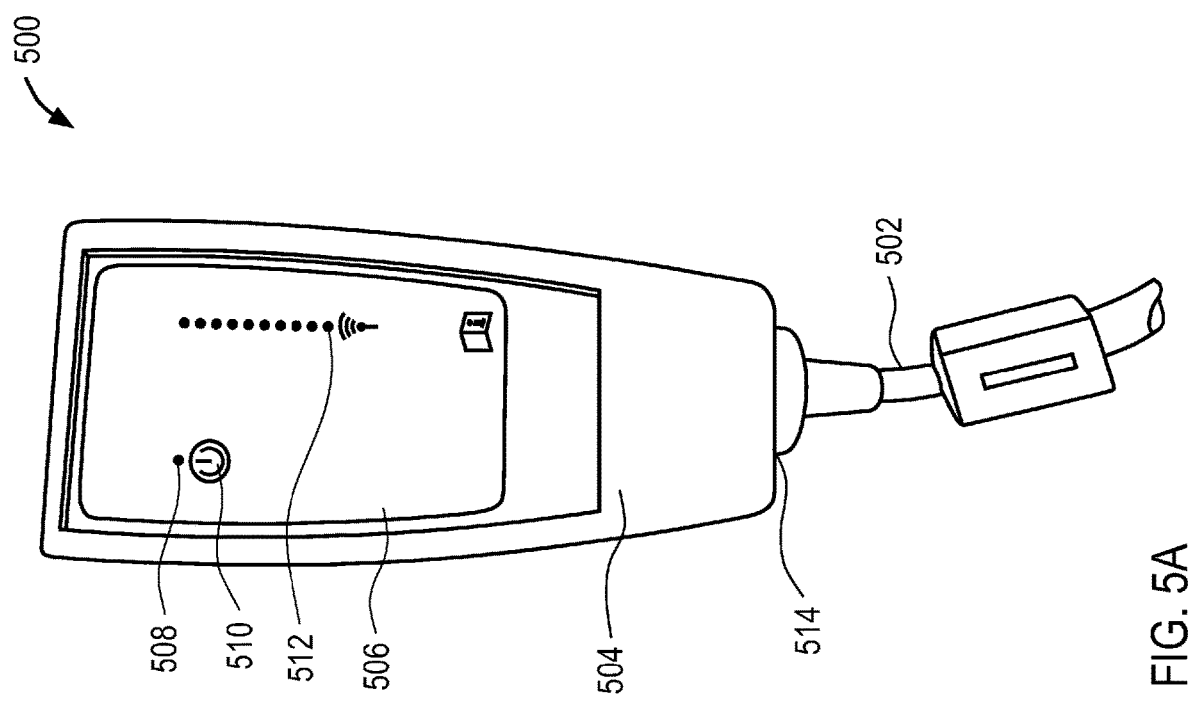
FIG. 5A shows an exemplary external programmer of the stimulator system of FIG. 1.

Referring now to FIG. 5A, exemplary external programmer 500 is now described. External programmer 500 includes housing 504 sized for handheld use and user interface 506. User interface 506 permits a user, e.g., patient, physician, caregiver, to send programming data to IPG 300 including commands to adjust stimulation parameters. Illustratively, user interface 506 includes status LED 508, status button 510, and signal LEDs 512. Status LED 508 is configured to illuminate when status button 510 is pressed to indicate a successful communication has been sent to IPG 300, e.g., command to stop a treatment session. Signal LEDs 512 are configured to illuminate based on the strength of the signal between IPG 300 and external programmer 500. The controller of external programmer 500 may direct appropriate signal LEDs 512 to illuminate based on the strength of the signals between the respective telemetry systems and coils or transceivers and antennas of external programmer 500 and IPG 300. Signal LEDs 512 may include diodes with different colors. For example, signal LEDs 512 may include red diodes configured to illuminate when the signal strength between external programmer 500 and IPG 300 is weak or non-existent, yellow diodes configured to illuminate when the signal strength between external programmer 500 and IPG 300 is medium, and green diodes configured to illuminate when the signal strength between external programmer 500 and IPG 300 is strong. External programmer 500 further includes port 514 configured to receive cable 502 such that external programmer 500 is electrically coupled and may communicate programming data with software-based programming system 600 run on a computer.

Figure 5B:
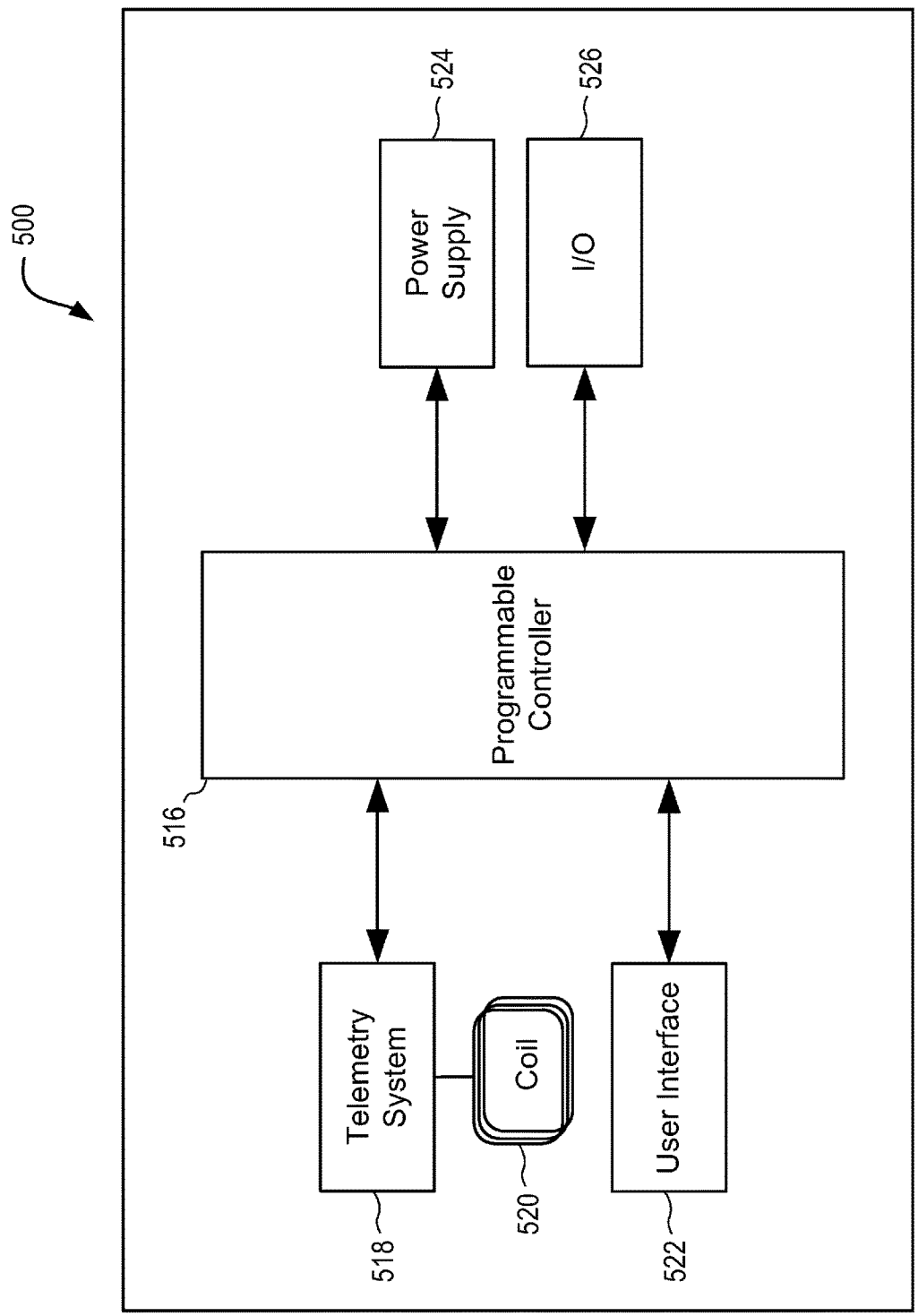
FIGS. 5B and 5C show alternative generalized block diagrams of the external programmer of FIG. 5A, wherein the external programmer of FIG. 5B has an inductive communications circuit and the external programmer of FIG. 5C has a RF transceiver communications circuit.

With respect to FIG. 5B, a generalized schematic diagram of the internal functional components of external programmer 500 is now described. External programmer 500 may include programmable controller 516, telemetry system 518 coupled to coil 520, user interface 522, power supply 524, and input and output circuitry (I/O) 526.

Controller 516 is electrically coupled to, and configured to control, the internal functional components of external programmer 500. Controller 516 may comprise a commercially available microcontroller unit including a programmable microprocessor, volatile memory, nonvolatile memory such as EEPROM for storing programming, and nonvolatile storage, e.g., Flash memory, for storing firmware and a log of system operational parameters and patient data. The memory of controller 516 may store program instructions that, when executed by the processor of controller 516, cause the processor and the functional components of external programmer 500 to provide the functionality ascribed to them herein. Controller 516 is configured to be programmable such that stimulation parameters, e.g., pulse amplitude (voltage or current), pulse width, stimulation rate, stimulation frequency, ramp timing, cycle timing, session timing, and electrode configuration may be adjusted responsive to user input received at user interface 522. For example, controller 516 may send programming data responsive to user input received at user interface 522 to controller 318 of IPG 300 via the respective telemetry (or RF) systems to adjust stimulation parameters or to start or stop a treatment session. In a preferred embodiment, only a physician has access to external programmer 500 to minimize the chance of injury caused by adjustments made by non-physician users.

Controller 516 is coupled to telemetry system 518, which is electrically coupled to coil 520, that permits transmission of programming data, and optionally power, between software-based programming system 600 and IPG 300 (or IPG 300") via external programmer 500. In this manner, IPG 300 may be powered, programmed, and/or controlled by software-based programming system 600 and external programmer 500 responsive to user input received at user interface 522. For example, controller 516 may direct telemetry system 518 to transmit stimulation parameter(s) such as pulse amplitude (voltage or current), pulse width, stimulation rate, stimulation frequency, ramp timing, cycle timing, session timing, and electrode configuration, including commands to start or stop a treatment session, to IPG 300 responsive to user input received at user interface 522 and/or software-based programming system 600. As another example, controller 516 may direct telemetry system 518 to transmit interrogation commands such as requests for the actual value of stimulation parameter(s), battery voltage, data logged at IPG 300, and IPG 300 status data, to IPG 300 responsive to user input received at user interface 522 and/or software-based programming system 600, and to receive responses to the interrogation commands from IPG 300. As yet another example, controller 516 may direct telemetry system 518 to transmit commands to IPG 300 to calculate the impedance of electrode lead 200 using a routine stored on controller 318 of IPG 300 and to receive the calculated lead impedance from the telemetry system of IPG 300. The technology for telemetry system 518 and coil 520 is well known to one skilled in the art and may be similar to telemetry system 320 and coil 322 described above. Alternatively, coil 520 may be used to transmit power only, and separate radio frequency transmitters may be provided in external programmer 500 and IPG 300 for establishing directional data communication.

User interface 522 is configured to receive user input and to display information to the user. As described above, user interface 522 may include buttons for receiving user input and LEDs for displaying information to the user. As will be readily apparent to one skilled in the art, user interface 522 is not limited thereto and may use a display, a touch screen, a keypad, a microphone, a speaker, a trackball, or the like.

Power supply 524 powers the electrical components of external programmer 500, and may comprise a primary cell or battery, a secondary (rechargeable) cell or battery or a combination of both. Alternatively, power supply 524 may be a port to allow external programmer 524 to be plugged into a conventional wall socket for powering components. In one preferred embodiment, power supply 524 comprises a USB port and cable that enables external programmer 500 to be powered from a computer, e.g., via cable 502, running software-based programming system 600.

Input and output circuitry (I/O) 526 may include ports for data communication such as wired communication with a computer and/or ports for receiving removable memory, e.g., SD card, upon which program instructions or data related to external programmer 500 use may be stored. In one embodiment, I/O 526 comprises port 514, and corresponding circuitry, for accepting cable 502 such that external programmer 500 is electrically coupled to a computer running software-based programming system 600.

Figure 5C:
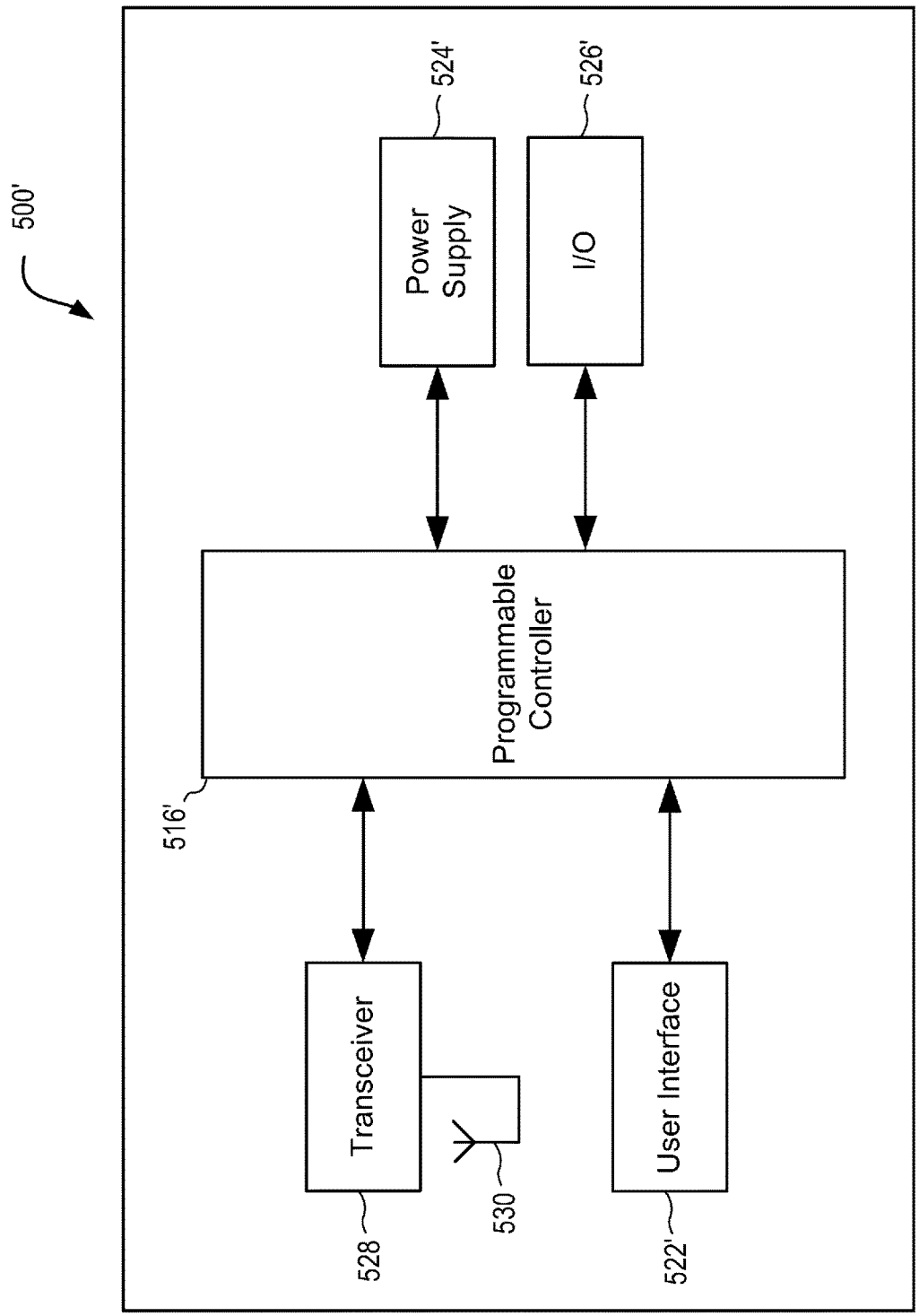

Referring to FIG. 5C, external programmer 500' is constructed similarly to external programmer 500 of FIG. 5B except that external programmer 500' includes a communications circuit employing transceiver 528 and antenna 530 rather than a communications circuit employing telemetry system 518 and coil 520. Transceiver 528 preferably comprises a radio frequency (RF) transceiver and is configured for bi-directional communications via antenna 530 with transceiver 332 via antenna 334 of IPG 300'. Transceiver 528 may transmit programming data from external programmer 500' to IPG 300' (or IPG 300"). For example, controller 516' may direct transceiver 528 to transmit stimulation parameter(s) such as pulse amplitude (voltage or current), pulse width, stimulation rate, stimulation frequency, ramp timing, cycle timing, session timing, and electrode configuration, including commands to start or stop a treatment session, to IPG 300' responsive to user input received at user interface 522' and/or software-based programming system 600. As another example, controller 516' may direct transceiver 528 to transmit interrogation commands such as requests for the actual value of stimulation parameter(s), battery voltage, data logged at IPG 300', and IPG 300' status data, to IPG 300' responsive to user input received at user interface 522' and/or software-based programming system 600, and to receive responses to the interrogation commands from IPG 300'. As yet another example, controller 516' may direct transceiver 528 to transmit commands to IPG 300' to calculate the impedance of electrode lead 200 using a routine stored on controller 318' of IPG 300' and to receive the calculated lead impedance from transceiver 332 of IPG 300'.

Transceiver 528 also may include a low power mode of operation, such that it periodically awakens to listen for incoming messages and responds only to those messages including the unique device identifier assigned to that external programmer. In addition, transceiver 528 may employ an encryption routine to ensure that messages sent from, or received by, external programmer 500' cannot be intercepted or forged.

Figure 6:
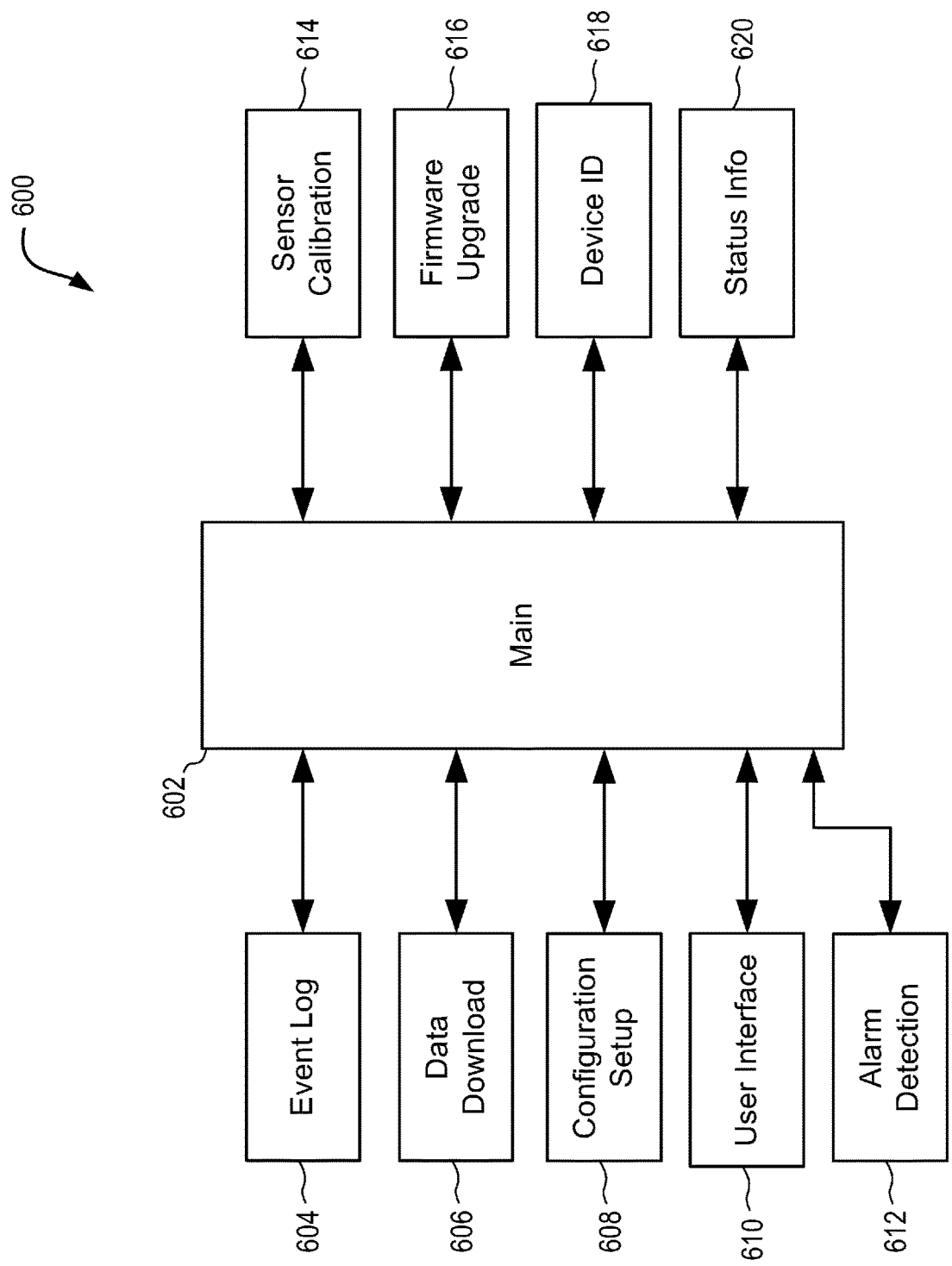
FIG. 6 is a block diagram of the functional components of an exemplary software-based programming system of the stimulator system of FIG. 1.

Referring now to FIG. 6, the software implementing programming system 600 is now described. The software of programming system 600 comprises a number of functional blocks, schematically depicted in FIG. 6, including main block 602, event logging block 604, data download block 606, configuration setup block 608, user interface block 610, alarm detection block 612, sensor calibration block 614, firmware upgrade block 616, device identifier block 618, and status information block 620. The software preferably is written in C++ and employs an object oriented format. In one preferred embodiment, the software is configured to run on top of a Microsoft Windows™ (a registered trademark of Microsoft Corporation, Redmond, Wash.) or Unix-based operating system, such as are conventionally employed on desktop and laptop computers. The computing device could also be a "smart phone" or tablet such as an iPad available from Apple Inc. of Cupertino, Calif., and other operating systems such as iOS or Android could be suitable foundations on which to build the software. The computer running programming system 600 preferably includes a data port, e.g., USB port or comparable wireless connection, that permits external programmer 500 and/or activator 400 to be coupled thereto. Alternatively, as discussed above, the computer may include a wireless card, e.g., conforming to the IEEE 802.11 standard, thereby enabling IPG 300, activator 400, and/or external programmer 500 to communicate wirelessly with the computer running programming system 600. As a further alternative, IPG 300, activator 400, and/or external programmer 500 may include a communications circuit(s) having telephony circuitry, e.g., GSM, CDMA, LTE circuitry, or the like, that automatically dials and uploads data, such as alarm data, from IPG 300 to a secure website accessible by the patient's physician.

Main block 602 preferably includes a main software routine that executes on the physician's computer, and controls overall operation of the other functional blocks. Main block 602 enables the physician to download event data and alarm information stored on IPG 300, via external programmer 500, to his office computer, and also permits programming system 600 to directly control operation of IPG 300, via external programmer 500. Main block also enables the physician to upload firmware updates and configuration data to IPG 300 via external programmer 500.

Event Log block 604 is a record of operational data downloaded from IPG 300, using external programmer 500, and may include, for example, treatment session start and stop times, current stimulation parameters, stimulation parameters from previous treatment sessions, sensor data, lead impedance, battery current, battery voltage, battery status, and the like. The event log also may include the occurrence of events, such as alarms or other abnormal conditions.

Data Download block 606 is a routine that commands IPG 300, using external programmer 500, to transfer data to programming system 600 for download after IPG 300 is coupled to the computer programming system 600 via external programmer 500. Data Download block 606 may initiate, either automatically or at the instigation of the physician via user interface block 610, downloading of data stored in the event log.

Configuration Setup block 608 is a routine that configures the parameters stored within IPG 300, using external programmer 500, that control operation of IPG 300. The interval timing parameters may determine, e.g., how long the processor remains in sleep mode prior to being awakened to listen for radio communications or to control IPG 300 operation. The interval timing parameters may control, for example, the duration of a treatment session. Interval timing settings transmitted to IPG 300 from programming system 600 also may determine when and how often event data is written to the memory in controller 318. In an embodiment in which external programmer 500 is also configured to transfer data to activator 400, programming system 600 also may be used to configure timing parameters used by the firmware executed by controller 426 of activator 400. Block 608 also may be used by the physician to configure parameters stored within the memory of controller 318 relating to limit values on operation of controller 318. These values may include times when IPG 300 may and may not operate, etc. Block 608 also may configure parameters store within the memory of controller 318 relating to control of operation of IPG 300. These values may include target numbers of treatment sessions and stimulation parameters.

User interface block 610 handles display of information retrieved from the programming system 600 and IPG 300, via external programmer 500, and data download block 606, and presents that information in an intuitive, easily understood format for physician review. Such information may include status of IPG 300, treatment session start and stop times, current stimulation parameters, stimulation parameters from previous treatment sessions, sensor data, lead impedance, battery status, and the like. User interface block 610 also generates user interface screens that permit the physician to input information to configure the session timing, stimulation parameters, requests to calculate lead impedance, etc. As will be readily understood by one of ordinary skill in the art, a user may enter data into the user interface using suitable mechanisms known in the art, such as, entering numbers, letters, and/or symbols via a keyboard or touch screen, mouse, touchpad, selection from a drop-down menu, voice commands, or the like.

Alarm detection block 612 may include a routine for evaluating the data retrieved from IPG 300, using external programmer 500, and flagging abnormal conditions for the physician's attention. For example, alarm detection block 612 may flag when a parameter measured by system sensors 328 is above or below a predetermined threshold.

Sensor calibration block 614 may include a routine for testing or measuring drift, of system sensors 328 employed in IPG 300, e.g., due to aging or change in humidity. Block 614 may then compute offset values for correcting measured data from the sensors, and transmit that information to IPG 300 for storage in the nonvolatile memory of controller 318.

Firmware upgrade block 616 may comprise a routine for checking the version numbers of the controller firmware installed on IPG 300, using external programmer 500, and identify whether upgraded firmware exists. If so, the routine may notify the physician and permit the physician to download revised firmware to IPG 300, in nonvolatile memory.

Device identifier block 618 consists of a unique identifier for IPG 300 that is stored in the nonvolatile memory of controller 318 and a routine for reading that data when programming system 600 is coupled to IPG 300 via external programmer 500. The device identifier also may be used by IPG 300 to confirm that wireless communications received from activator 400 and/or external programmer 500 are intended for that specific IPG. Likewise, this information is employed by activator 400 and/or external programmer 500 to determine whether a received message was generated by the IPG associated with that system. Finally, the device identifier information may be employed by programming system 600 to confirm that activator 400 and IPG constitute a matched set.

Status information block 620 comprises a routine for interrogating IPG 300, when connected via activator 400, or external programmer 500 and programming system 600, to retrieve current status data from IPG 300, using external programmer 500. Such information may include, for example, battery status, stimulation parameters, lead impedance, the date and time on the internal clocks of treatment sessions, version control information for the firmware and hardware currently in use, and sensor data.

Figure 7A:
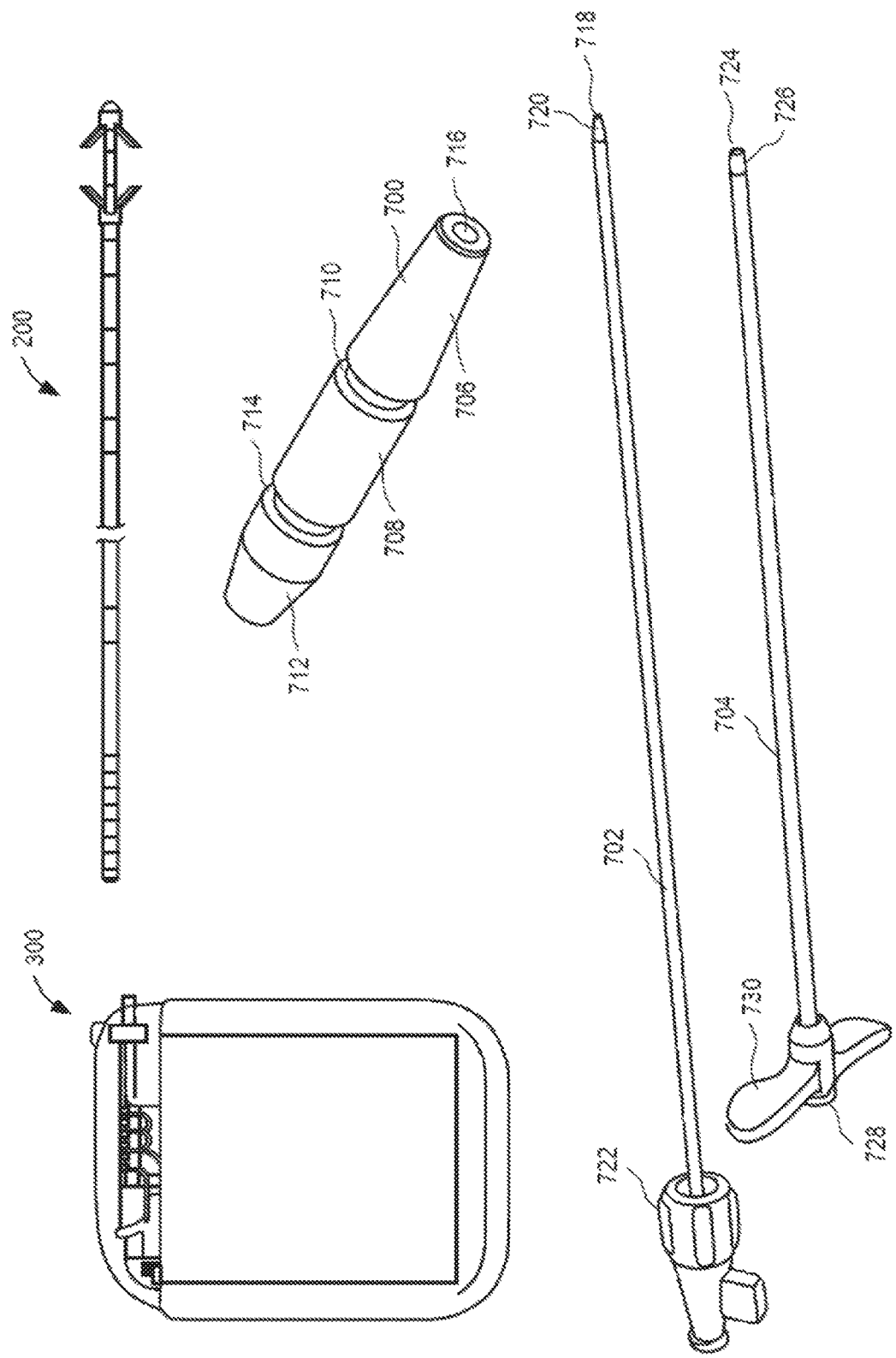
FIGS. 7A through 7D show an exemplary method for implanting an electrode lead and IPG in accordance with the principles of the present invention.

Referring now to FIGS. 7A to 7D, an exemplary method for implanting an electrode lead and IPG is described. First, electrode lead 200, IPG 300, stylet (now shown), suture sleeve 700, introducer 702, and dilator 704 are provided, as shown in FIG. 7A. In FIG. 7A, components of the system are not depicted to scale on either a relative or absolute basis. Suture sleeve 700 illustratively includes first end section 706, middle section 708 separated from first end section by first groove 710, second end section 712 separated from middle section 708 by second groove 714, and sleeve lumen 716. First and second end sections 706 and 712 may have truncated conical portions as shown. First and second grooves 710 and 714 are sized and shaped to accept sutures such that suture sleeve 700 may be secured to tissue, e.g., superficial fascia, using the sutures. Sleeve lumen 716 is sized such that electrode lead 200 may be inserted therethrough.

Introducer 702 may include introducer lumen 718, distal tip 720, and coupling portion 722. Introducer lumen 718 extends through introducer 702 and is shaped and sized to permit electrode lead 200 to slide therethrough. Distal tip 720 is beveled to ease introduction through tissue. Coupling portion 722, illustratively a female end with threads, is configured to be coupled to a portion of dilator 704. In one embodiment, introducer 702 comprises a commercially available 7 French (Fr) introducer.

Dilator 704 may include dilator lumen 724, distal tip 726, coupling portion 728, and handle 730. Dilator lumen 724 extends through dilator 704 and is shaped and sized to permit introducer 702 to slide therethrough. Distal tip 726 is beveled to ease introduction through tissue. Coupling portion 728, illustratively a male end with threads, is configured to be coupled to a portion of introducer 702, e.g., coupling portion 722. Handle 730 is sized and shaped to permit a physician to comfortably hold dilator 704.

Next, a stylet is inserted within the stylet lumen of electrode lead 200 to provide additional stiffness to electrode lead 200 to ease passage of electrode lead 200 through introducer 702. The stylet may be a commercially available stylet such as a locking stylet available from Cook Group Incorporated of Bloomington, Ind. Electrode lead 200 then is inserted within introducer lumen 718 of introducer 702.

Using fluoroscopy, acoustic, anatomic, or CT guidance, dilator 704 is delivered through the skin and optionally through muscles and/or other anatomical structures on the path to a target site, e.g., in or adjacent to tissue associated with control of the lumbar spine. Such tissue may include nervous tissue, muscle, ligament, and/or joint capsule. In one embodiment, muscle includes skeletal muscle such as the multifidus, transverse abdominis, quadratus lumborum, psoas major, internus abdominis, obliquus externus abdominis, and erector spinae muscles and nervous tissue includes a peripheral nerve that innervates skeletal muscle. In a preferred embodiment, nervous tissue comprises the medial branch of the dorsal ramus nerve, or fascicles thereof, that innervate the multifidus muscle.

Next, introducer 702 (having a portion of the electrode lead disposed therein) is inserted through dilator lumen 724 to the target site. Introducer 702 may then be coupled to dilator 704, e.g., by screwing coupling portion 722 onto coupling portion 728.

Figure 7B:
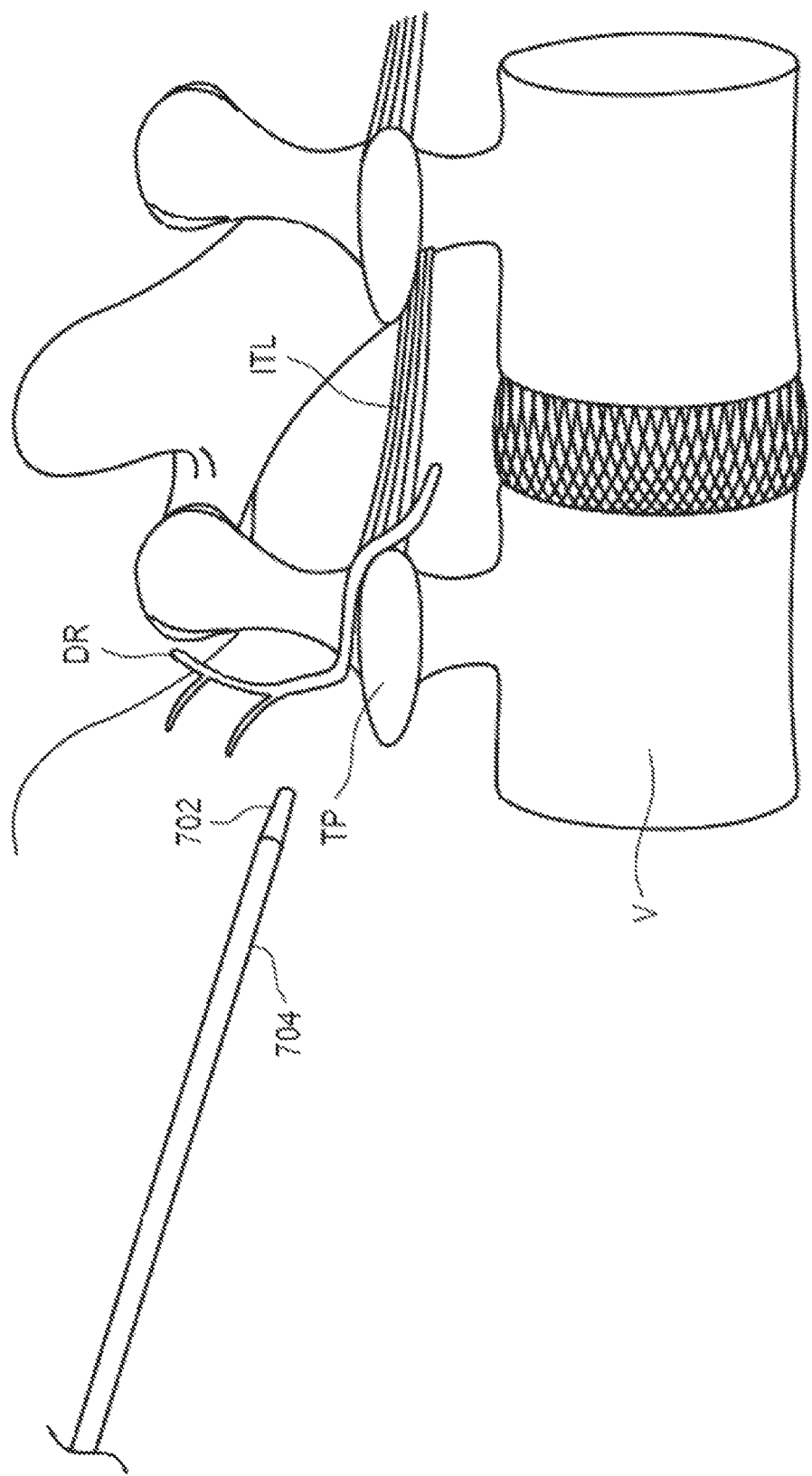
Figure 7C:
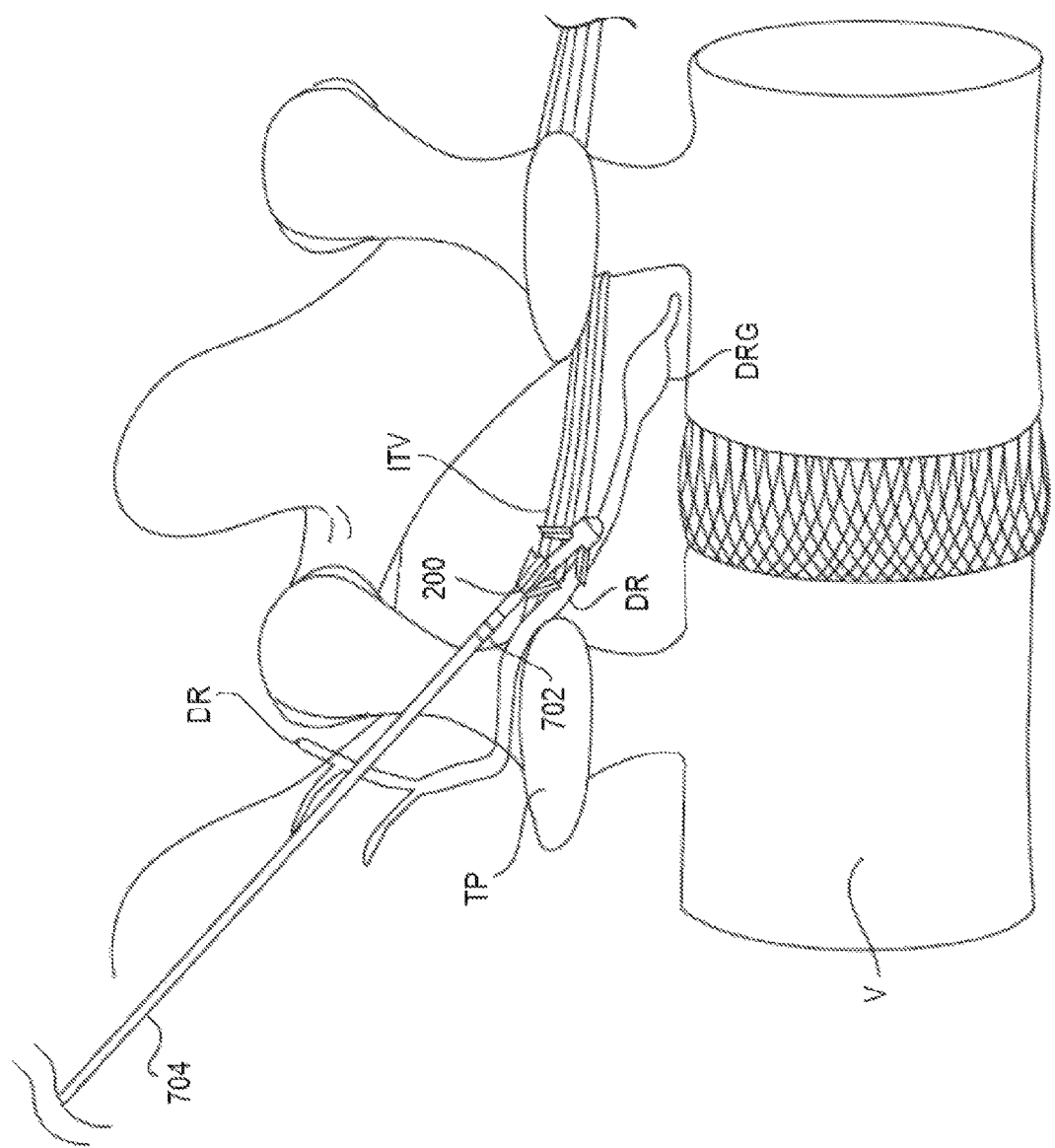
Figure 7D:
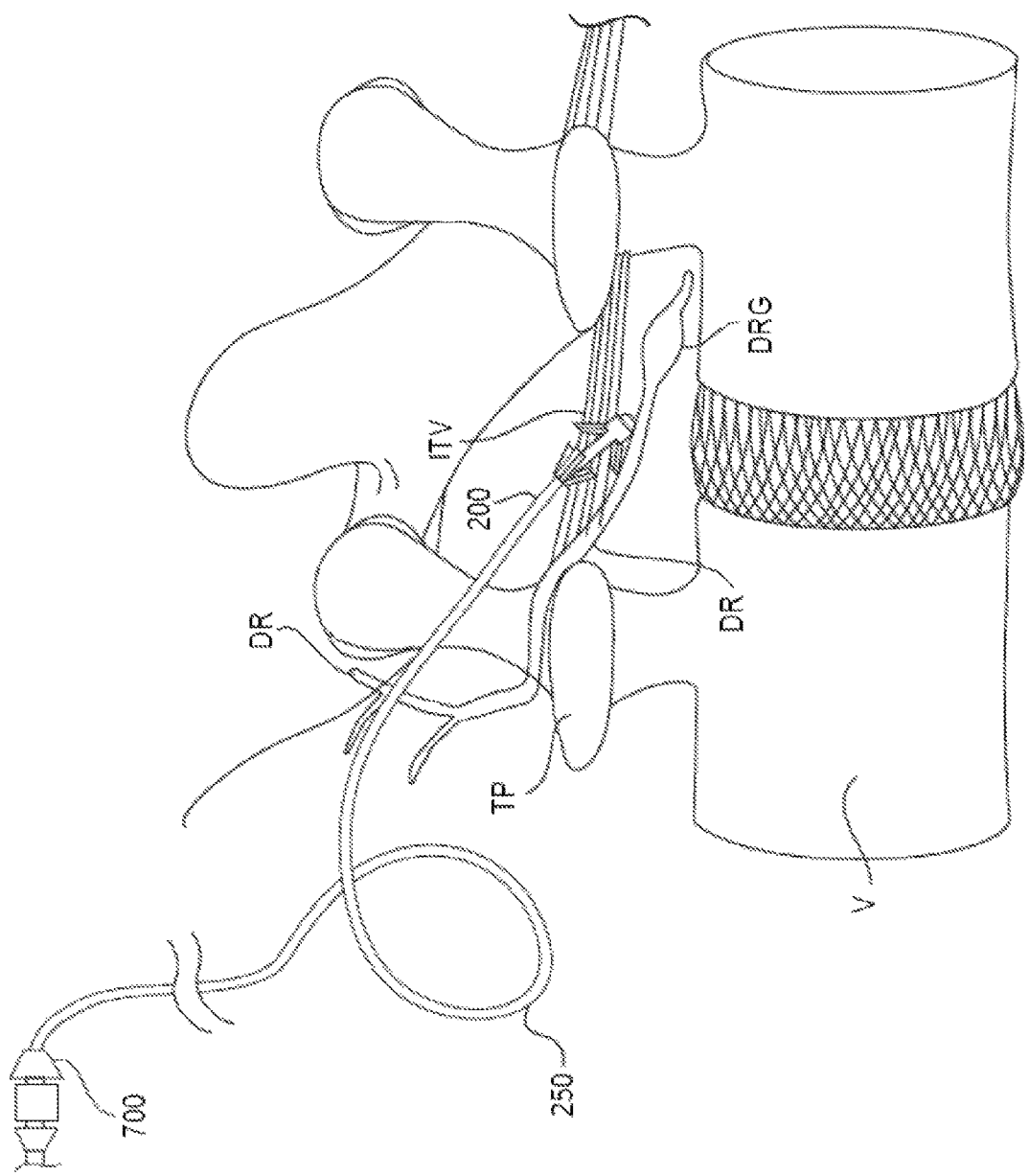

FIGS. 7B-7D depict a lateral projection of a segment of a typical human lumbar spine shown having a vertebral body V, transverse process TP, inter-transverse ligament ITL, and a dorsal ramus DR. In FIG. 7B, dilator 704 having introducer 702 disposed therethrough, which has a portion of the electrode lead disposed therein, are positioned adjacent to the target site, illustratively, the medial branch of the dorsal ramus DR nerve that innervates the multifidus muscle. In one embodiment, electrodes of the electrode lead are positioned to stimulate the medial branch of the dorsal ramus that exits between the L2 and L3 lumbar segments and passes over the transverse process of the L3 vertebra, thereby eliciting contraction of fascicles of the lumbar multifidus at the L3, L4, L5 and Si segments and in some patients also at the L2 segment.

Introducer 702 and dilator 704 are moved proximally, e.g., using handle 730, while maintaining the position of electrode lead 200 at the target site, as shown in FIG. 7C. The first and second fixation elements of electrode lead 200 individually transition from a collapsed state within introducer 702 to an expanded state, shown in FIG. 7C, as introducer 702 passes over the respective fixation element. The first and second fixation elements sandwich an anchor site, e.g., muscle, therebetween without damaging the anchor site in the expanded state to fix electrode lead 200 at the target site.

Introducer 702 and dilator 704 are moved proximally off the proximal end of electrode lead 200 and suture sleeve 700 is placed over the proximal end of electrode lead 200 and moved distally, as illustrated in FIG. 7D. When suture sleeve 700 is positioned adjacent to the superficial fascia SF beneath skin SK, sutures are sewn into the first and second grooves of suture sleeve 700 to secure suture sleeve 700 to the superficial fascia SF.

As shown in FIG. 7D, electrode lead 200 may include strain relief portion 250 as described below. Strain relief portion 250 is configured to reduce lead dislodgement and/or fracture after implantation due to, for example, the lack of suitable anchor sites for the electrode leads, the torsional and/or bending stresses imposed on the electrode leads by movement of the surrounding muscles. As described below, strain relief portion 250 may take on a variety of structures that are designed to reduce the strain on electrode lead 200 and the fixation elements, thereby reducing the risk of lead dislodgement, fatigue fracture, and injury to the nervous tissue through which electrode lead 200 passes. In the embodiment of FIG. 7D, strain relief portion 250 comprises a loop. Preferably, the loop comprises a diameter of at least 2 cm. In an alternative embodiment, strain relief portion 250 comprises a "C" shape. Other strain relief structures designed to reduce the strain on electrode lead 200 and the fixation elements of the present invention may be used, such as those described in U.S. Patent Application Pub. No. 2014/0350653 to Shiroff, assigned to the assignee of the present invention, the entire contents of which are incorporated herein by reference. Strain relief portion 250 permits extension of electrode lead 200 between proximal end 224 and distal end 211 of electrode lead 200 without imposing excessive loads on the fixation elements that could result in axial displacement of the electrodes.

Finally, the IPG is coupled to the proximal end of electrode lead 200 and implanted within the lower back of the patient, or other anatomically suitable location such as the buttocks or flank.

Exemplary stimulation parameters in accordance with aspects of the present invention are now described. Preferably, such stimulation parameters are selected and programmed to induce contraction of muscle to restore neural control and rehabilitate muscle associated with control of the spine, thereby improving lumbar spine stability and reducing back pain. As used in this specification, "to restore muscle function" means to restore an observable degree of muscle function to provide improvement as recognized by existing measures of patient assessment, such as the Oswestry Disability Index ("ODI") as described in Lauridsen et al., *Responsiveness and minimal clinically important difference for pain and disability instruments in low back pain patients*, BMC Musculoskeletal Disorders, 7: 82-97 (2006), the European Quality of Life Assessment 5D ("EQ-5D") as described in Brazier et al., *A comparison of the EQ-5D and SF-6D across seven patient groups*, Health Econ. 13: 873-884 (2004), or a Visual Analogue Scale ("VAS") as described in Hagg et al., *The clinical importance of changes in outcome scores after treatment for chronic low back pain*, Eur Spine J 12: 12-20 (2003). In accordance with one aspect of the present invention, "to restore muscle function" means to observe at least a 15% improvement in one of the foregoing assessment scores within 30-60 days of initiation of treatment. As described above, the stimulation parameters may be programmed into the IPG, may be adjusted in the IPG responsive to (i) stimulation commands transferred from the activator or (ii) programming data transferred from the external programmer.

The stimulation parameters include, for example, pulse amplitude (voltage or current), pulse width, stimulation rate, stimulation frequency, ramp timing, cycle timing, session timing, and electrode configuration, including commands to start or stop a treatment session. In one embodiment, pulse amplitude is programmed to be adjustable between 0 and 7 mA. In a preferred embodiment, pulse amplitude is programmed to be between about 2-5 mA, 2.5-4.5 mA, or 3-4 mA, and preferably about 3.5 mA. In one embodiment, pulse width is programmed to be adjustable between 25 and 500 µs. In a preferred embodiment, pulse width is programmed to be between about 100-400 µs, 150-350 µs, or 200-300 µs, and preferably about 350 µs. In one embodiment, stimulation rate is programmed to be adjustable between 1 and 40 Hz. In a preferred embodiment, stimulation rate is programmed to be between about 1-20 Hz, 5-35 Hz, 10-30 Hz, or 15-20 Hz, and preferably about 20 Hz. In one embodiment, on ramp timing is programmed to be adjustable between 0 and 5 s. In a preferred embodiment, on ramp timing is programmed to be between about 0.5-4.5 s, 1-4 s, 1.5-3.5 s, or 2-3 s, and preferably about 2.5 s. In one embodiment, off ramp timing is programmed to be adjustable between 0 and 5 s. In a preferred embodiment, off ramp timing is programmed to be between about 0.5-4.5 s, 1-4 s, 1.5-3.5 s, or 2-3 s, and preferably about 2.5 s. In one embodiment, cycle-on timing is programmed to be adjustable between 2 and 20 s. In a preferred embodiment, cycle-on timing is programmed to be between about 4-18 s, 6-16 s, 8-14 s, 9-13 s, or 10-12 s and preferably about 10 s. In one embodiment, cycle-off timing is programmed to be adjustable between 20 and 120 s. In a preferred embodiment, cycle-off timing is programmed to be between about 30-110 s, 40-100 s, 50-90 s, 55-85 s, 60-80 s, or 65-75 s and preferably about 70 s. In one embodiment, session timing is programmed to be adjustable between 1 and 60 min. In a preferred embodiment, session timing is programmed to be between about 5-55 min, 10-50 min, 15-45 min, 20-40 min, or 25-35 min, and preferably about 30 min.

Figure 8:
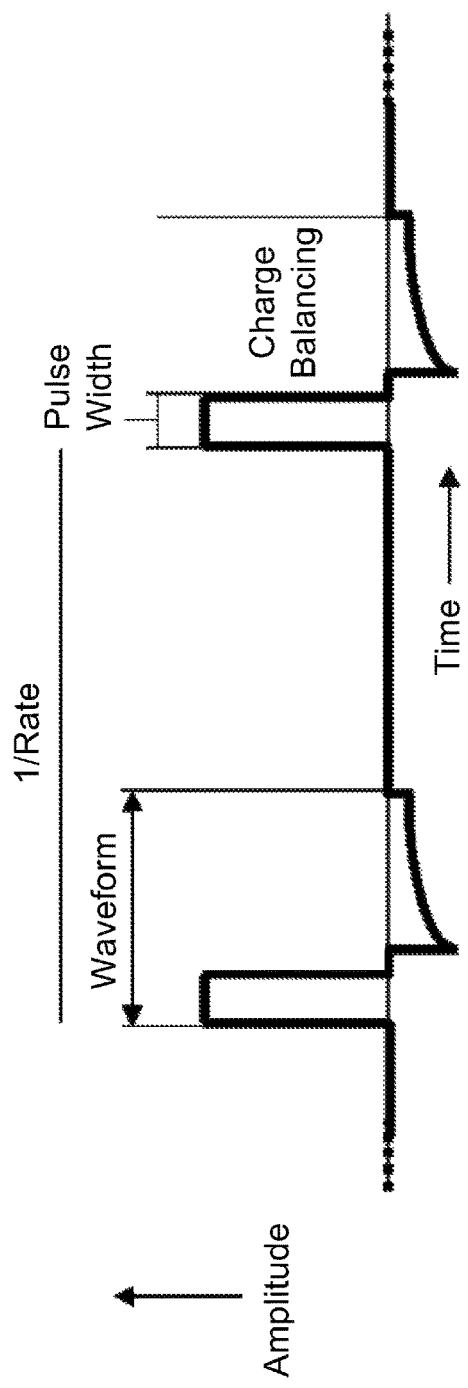
FIG. 8 shows a graph depicting an exemplary charge-balanced electrical stimulation waveform that may be delivered by the electrodes and IPG of the present invention.

FIG. 8 is a graph of an exemplary charge-balanced electrical stimulation waveform that may be delivered by the electrodes and IPG of the present invention. The IPG directs the electrodes, responsive to programming, stimulation commands, and/or received programming data, to stimulate at a pulse amplitude for the time of a pulse width and then balances the charge by dropping to a negative pulse amplitude and then bringing the pulse amplitude back to zero over the time of a waveform. The stimulation may be current-controlled and charge-balanced, or voltage-controlled and charge-balanced.

Figure 9:
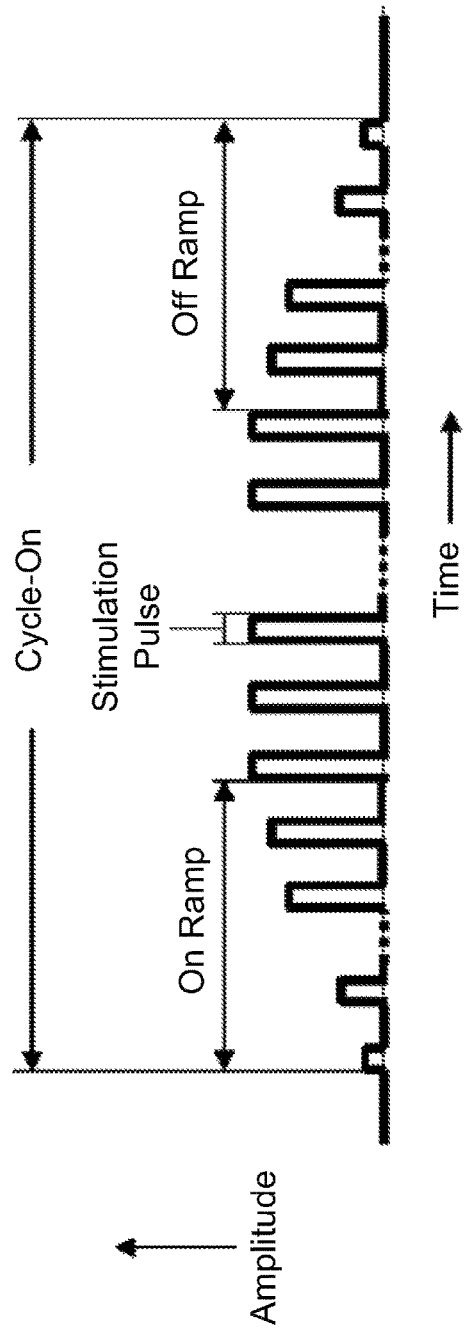
FIG. 9 shows a graph depicting an exemplary stimulation pulse train that may be delivered by the electrodes and IPG of the present invention.

FIG. 9 is a graph showing an exemplary stimulation pulse train that may be delivered by the electrodes and IPG of the present invention. During cycle-on programming, the IPG directs the electrodes, responsive to programming, stimulation commands, and/or received programming data, to deliver a stimulation pulse train in an "on ramp" manner such that the pulse amplitude increases in predetermined increments to reach the programmed peak pulse amplitude. In this way, the number of pulses in the "on ramp" needed to reach the programmed peak pulse amplitude may be determined by the IPG responsive to data supplied by the programming system. After reaching the programmed peak pulse amplitude, the IPG directs the electrodes to deliver at the programmed peak pulse amplitude for a predetermined number of stimulation pulses. After the predetermined number of stimulation pulses is reached, the IPG directs the electrodes, responsive to programming, stimulation commands, and/or received programming data, to deliver a stimulation pulse train in an "off ramp" manner such that the pulse amplitude decreases in predetermined increments from the programmed peak pulse amplitude to zero. As shown in FIG. 9, the pulse amplitude may drop, e.g., to zero, between each stimulation pulse.

Figure 10:
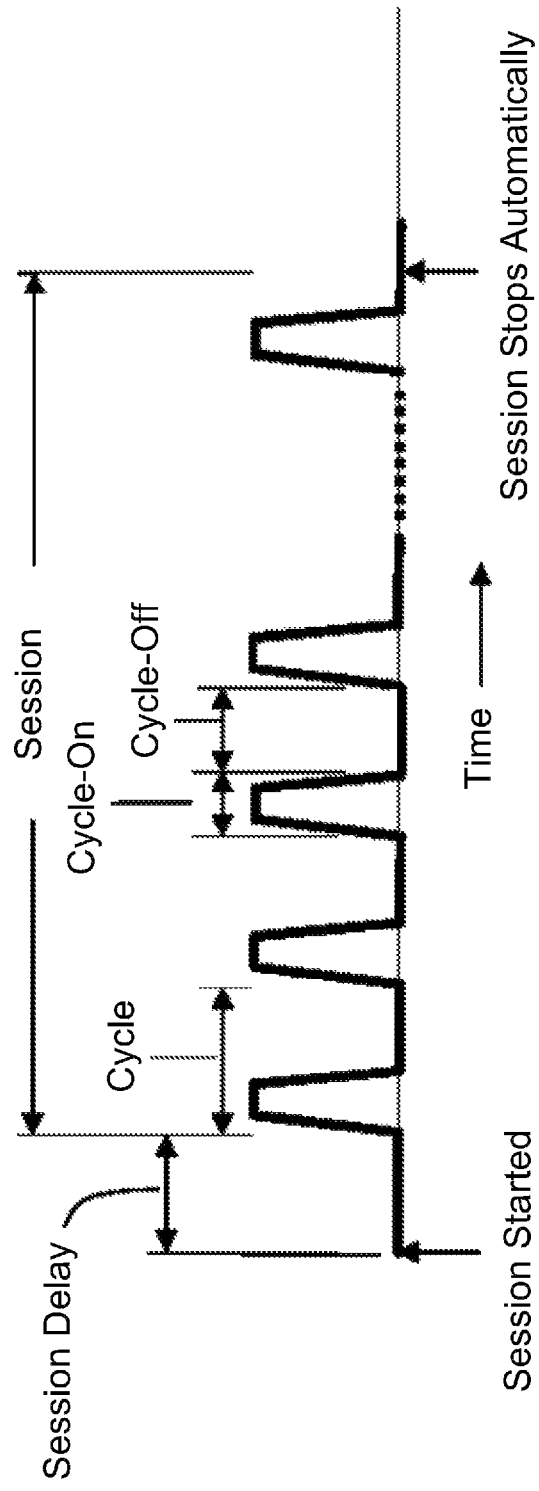
FIG. 10 shows a graph depicting an exemplary session that may be delivered by the electrodes and IPG of the present invention.

FIG. 10 is a graph showing an exemplary session that may be delivered by the electrodes and IPG of the present invention. In this example, during a cycle, the IPG directs the electrodes, responsive to programming, stimulation commands, and/or received programming data, to deliver electrical stimulation for the cycle-on duration, followed by a cycle-off duration of no electrical stimulation. Illustratively, a session is a programmable duration of repetitive cycles and the session delay is the time delay between the receipt of the command by the IPG to start a session to the start of the first cycle. After a session is completed, IPG directs the electrodes, responsive to programming, stimulation commands, and/or received programming data, to stop delivering electrical stimulation until a new session begins.

As will be readily understood by one of ordinary skill in the art, a user may enter data into the user interface using suitable mechanisms known in the art, such as, entering numbers, letters, and/or symbols via a keyboard or touch screen, mouse, touchpad, selection from a drop-down menu, voice commands, or the like.

Figure 11:
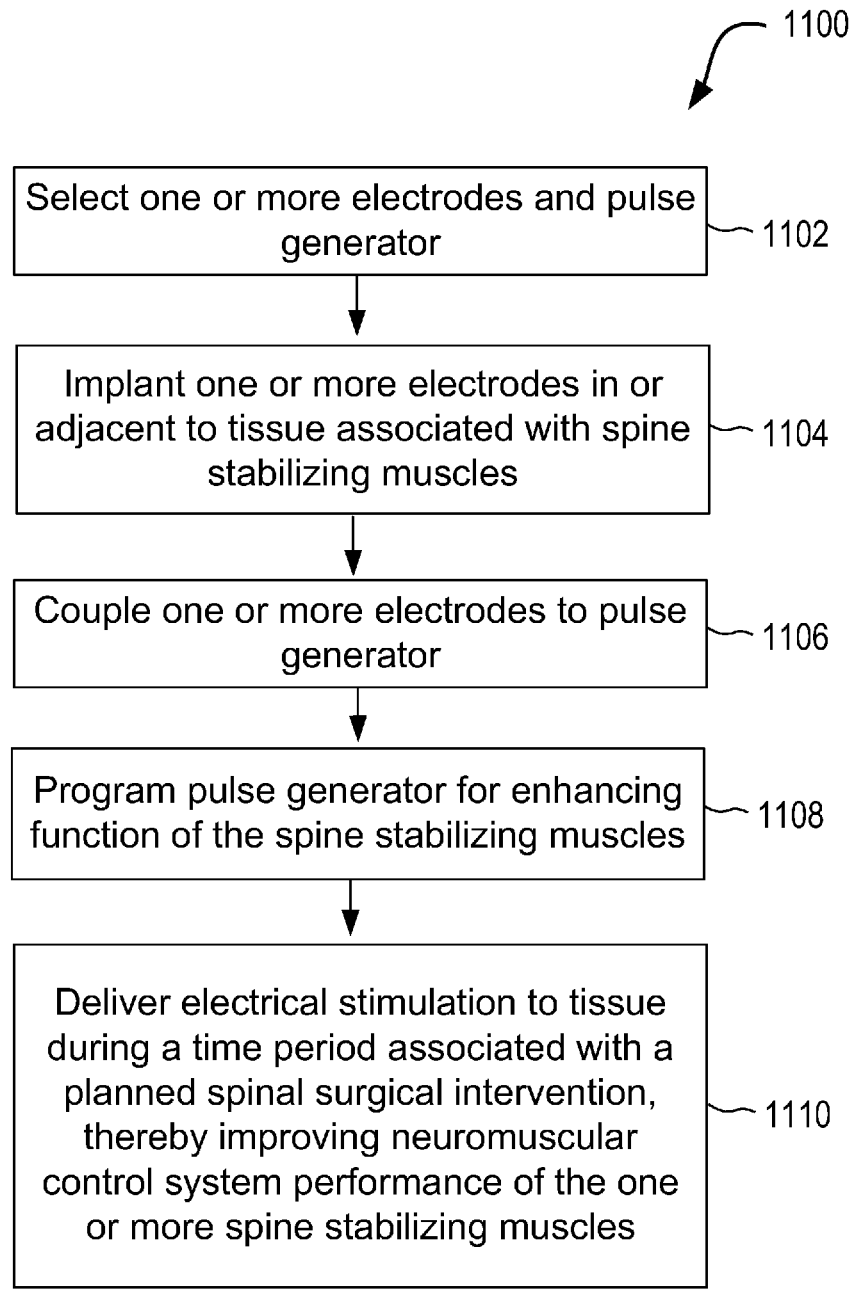
FIG. 11 illustrates a flow chart of an exemplary method for enhancing muscle function of spine stabilizing muscles in connection with a planned spine surgery intervention in a patient's back.

Referring now to FIG. 11, exemplary method 1100 for enhancing function of spine stabilizing muscles in connection with a planned spine surgery intervention in a patient's back is described. For example, spine stabilizing muscle function may be enhanced prior to or following the planned spine surgery intervention in accordance with exemplary method 1100. At step 1102, the physician selects one or more electrodes and a pulse generator. The one or more electrodes may be disposed on an electrode lead, such as electrode lead 200 of FIG. 2A or electrode lead 200' of FIG. 2B described above. The pulse generator may be external or implantable such as IPG 300 of FIG. 3A described above. At step 1104, the one or more electrodes are implanted in or adjacent to tissue associated with one or more spine stabilizing muscles. For example, the one or more electrodes may be implanted using the tools and method steps described above with reference to FIGS. 7A-7D or using the systems and methods described in U.S. Patent Application Pub. No. 2018/0008311 to Shiroff, assigned to the assignee of the present invention, the entire contents of which are incorporated herein by reference.

At step 1106, the pulse generator is electrically coupled to the one or more electrodes. This coupling may be done before or after the electrodes are implanted. Optionally, the pulse generator may be implanted at step 1106. For example, the pulse generator may be implanted and coupled to the one or more electrodes using the tools and methods described with reference to FIGS. 7J and 7K in U.S. Pat. No. 9,950,159 to Beck, assigned to the assignee of the present invention, the entire contents of which are incorporated herein by reference.

In accordance with one aspect of the present invention, the physician performs steps 1102, 1104, and 1106 a period prior to the planned spine surgery intervention, such that the electrical stimulation therapy may be delivered for a sufficient amount of time to improve neuromuscular control system performance of and strengthen the one or more spine stabilizing muscles as described in further detail below. The period of time prior to the planned spine surgery intervention may be predetermined, e.g., at least 30 days and/or less than 60 days. Alternatively, the physician performs steps 1102, 1104, and 1106 during the planned spine surgery intervention, thereby reducing the number of operations and permitting improvement of neuromuscular control system performance following the planned spine surgery intervention via electrical stimulation. In accordance with yet another aspect of the present invention, the physician performs steps 1102, 1104, and 1106 at some time after the planned spine surgery intervention if, for example, recovery wasn't going as expected.

At step 1108, the pulse generator is programmed with programming data received from an external programmer, e.g., external programmer 500 of FIG. 5A, for enhancing function of the spine stabilizing muscles. At step 1110, the pulse generator delivers electrical stimulation to the tissue associated with the spine stabilizing muscles via the one or more electrodes in accordance with the programming data, thereby improving neuromuscular control system performance of the one or more spine stabilizing muscles. The stimulation of the tissue may also strengthen the patient's spine stabilizing muscles such that the muscles are better able to withstand iatrogenic injury caused during the spine surgery intervention.

Electrical stimulation may be delivered, for example, to nervous tissue associated with the one or more spine stabilizing muscles. For example, electrical stimulation may be delivered to the medial branch of the dorsal ramus nerve, or fascicles thereof, innervating the multifidus muscle such that electrical stimulation causes contraction of the multifidus muscle. The pulse generator may deliver electrical stimulation in response to a command received by activator 400 of FIG. 4A, external programmer 500 of FIG. 5A, and/or software implementing programming system 600 of FIG. 6, as described above. The electrical stimulation therapy is provided via the one or more electrodes and the pulse generator for a treatment period sufficient for enhancing function of the spine stabilizing muscles prior to the planned spine surgery intervention. Such muscle enhancement prior to the planned spine surgery intervention via electrical stimulation is expected to improve performance of the spine stabilizing muscle(s) to improve spinal stability, thereby reducing recovery time of the patient post-back surgery. Such "prehab" is further expected to reduce back pain before and even after the surgery. The treatment period of electrical stimulation may be, for example, between 30-60 days prior to the planned spine surgery intervention. As will be understood by one of ordinary skill in the art, the treatment period may be longer than 60 days. Accordingly, the neural control and function of the patient's spine stabilizing muscles will be enhanced as a result of the prehab treatment such that the patient's recovery time following the planned spine surgery intervention will be reduced.

In accordance with one aspect of the present invention, the one or more electrodes may be removed prior to or during the planned spine surgery intervention. Accordingly, the one or more electrodes may be replaced during the surgical intervention, or alternatively, additional electrodes may be implanted at some time after the planned spine surgery intervention, e.g., if the patient's recovery from the surgical intervention is not going as well as expected.

In accordance with another aspect of the present invention, step 1104 may be performed prior to a planned surgical intervention, such that during step 1106, the one or more electrodes are coupled to an external pulse generator. Accordingly, during step 1110, the external pulse generator delivers electrical stimulation to the tissue associated with the spine stabilizing muscles via the one or more electrodes in accordance with the programming data, thereby improving neuromuscular control system performance of the one or more spine stabilizing muscles. Then, during the planned spine surgery intervention, the one or more electrodes may be decoupled from the external pulse generator and coupled to an implantable pulse generator which is implanted during the planned spine surgery intervention. This avoids the needs for two major surgical procedures.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A method for enhancing function of spine stabilizing muscles in connection with a spine surgery intervention in a patient's back, the method comprising:

selecting one or more electrodes and a pulse generator configured for electrical communication with the one or more electrodes;

implanting the one or more electrodes in or adjacent to tissue associated with one or more spine stabilizing muscles associated with local segmental control of a lumbar spine within a back of a patient;

programming the pulse generator for enhancing function of the one or more spine stabilizing muscles; and delivering, adjunctive to the spine surgery intervention, electrical stimulation from the pulse generator to the tissue associated with the one or more spine stabilizing muscles via the one or more electrodes to improve neuromuscular control system performance of the one or more spine stabilizing muscles in connection with the spine surgery intervention to facilitate rehabilitation and improve the function of the one or more spine stabilizing muscles after the spine surgery intervention.

2. The method of claim 1, wherein implanting the one or more electrodes in or adjacent to tissue associated with one or more spine stabilizing muscles comprises implanting the one or more electrodes in or adjacent to a dorsal ramus nerve that innervates the multifidus muscle, and wherein delivering electrical stimulation comprises delivering electrical stimulation from the pulse generator to the dorsal ramus nerve that innervates the multifidus muscle.

3. The method of claim 1, wherein the one or more spine stabilizing muscles comprises at least one of a multifidus, transverse abdominis, quadratus lumborum, psoas major, internus abdominis, obliquus externus abdominis, or erector spinae muscles.

4. The method of claim 1, wherein the one or more electrodes are disposed on an electrode lead, the electrode lead having a first anchor angled distally relative to the electrode lead and a second anchor distal to the first anchor angled proximally relative to the electrode lead, and wherein implanting the one or more electrodes in or adjacent to tissue associated with one or more spine stabilizing muscles comprises anchoring the electrode lead in or adjacent to tissue associated with one or more spine stabilizing muscles via the first and second anchors.

5. The method of claim 1, wherein programming the pulse generator further comprises transmitting programing data from an external programmer to the pulse generator, wherein delivering electrical stimulation from the pulse generator to the tissue associated with the one or more spine stabilizing muscles comprises delivering electrical stimulation consistent with the programming data.

6. The method of claim 5, wherein the programming data comprises at least one of: pulse amplitude, pulse width, stimulation rate, stimulation frequency, ramp timing, cycle timing, session timing, or electrode configuration.

7. The method of claim 1, wherein delivering electrical stimulation from the pulse generator to the tissue associated with the one or more spine stabilizing muscles causes contraction of the one or more spine stabilizing muscles.

8. The method of claim 1, wherein delivering electrical stimulation from the pulse generator to the tissue associated with the one or more spine stabilizing muscles comprises delivering electrical stimulation at a stimulation rate between 1-30 Hz.

9. The method of claim 1, wherein delivering electrical stimulation from the pulse generator to the tissue associated with the one or more spine stabilizing muscles comprises delivering electrical stimulation at a pulse width between 20-500 μs.

10. The method of claim 1, wherein delivering electrical stimulation from the pulse generator to the tissue associated with the one or more spine stabilizing muscles comprises delivering electrical stimulation at a pulse amplitude between 0.1-7 mA.

11. The method of claim 1, wherein the pulse generator is configured to be percutaneously implanted, the method further comprising implanting the pulse generator prior to delivering electrical stimulation from the pulse generator to the tissue associated with the one or more spine stabilizing muscles via the one or more electrodes.

12. The method of claim 1, further comprising transmitting a stimulation command from an activator to the pulse generator, wherein delivering electrical stimulation from the pulse generator to the tissue associated with the one or more spine stabilizing muscles comprises delivering electrical stimulation responsive to the stimulation command.

13. The method of claim 12, wherein the stimulation command comprises at least one of: a command to start a treatment session or stop the treatment session; a command to provide a status of the pulse generator; or a request to conduct an impedance assessment.

14. The method of claim 1, further comprising sensing muscle contraction via one or more sensors coupled to the pulse generator, and adjusting the electrical stimulation delivered by the pulse generator to maintain smooth and continuous muscle contraction.

15. The method of claim 1, further comprising:
reprogramming the pulse generator for restoring muscle function of the one or more spine stabilizing muscles; and
delivering, according to the reprogramming and after the spine surgery intervention, electrical stimulation from the pulse generator to the tissue associated with the one or more spine stabilizing muscles via the one or more electrodes, thereby facilitating rehabilitation of the one or more spine stabilizing muscles after the spine surgery intervention.

* * * * *